(12) United States Patent
Walford et al.

(10) Patent No.: US 12,232,693 B2
(45) Date of Patent: Feb. 25, 2025

(54) SYSTEMS AND METHODS FOR AUTOMATICALLY CONTROLLING LOADING DOCK EQUIPMENT

(71) Applicant: ASSA ABLOY Entrance Systems AB, Landskrona (SE)

(72) Inventors: Brett A. Walford, Corinth, TX (US); Eric Breen, Clermont, FL (US)

(73) Assignee: ASSA ABLOY Entrance Systems AB, Landskrona (SE)

( * ) Notice: Subject to any disclaimer, the term of this patent is extended or adjusted under 35 U.S.C. 154(b) by 0 days.

(21) Appl. No.: 17/743,726

(22) Filed: May 13, 2022

(65) Prior Publication Data

US 2022/0338719 A1    Oct. 27, 2022
US 2025/0009207 A9    Jan. 9, 2025

Related U.S. Application Data

(63) Continuation of application No. 16/126,063, filed on Sep. 10, 2018, now Pat. No. 11,358,813, which is a
(Continued)

(51) Int. Cl.
*A61B 1/00* (2006.01)
*A61B 1/018* (2006.01)
(Continued)

(52) U.S. Cl.
CPC ...... *A61B 1/00098* (2013.01); *A61B 1/00066* (2013.01); *A61B 1/00181* (2013.01);
(Continued)

(58) Field of Classification Search
CPC ............ A61B 1/00098; A61B 1/00066; A61B 1/00181; A61B 1/018; A61B 1/051;
(Continued)

(56) References Cited

U.S. PATENT DOCUMENTS

| | | | |
|---|---|---|---|
| 1,775,909 A | 9/1930 | Mikkelsen | |
| 2,362,981 A | 11/1944 | Philemon | |

(Continued)

FOREIGN PATENT DOCUMENTS

| | | |
|---|---|---|
| CA | 2963656 A1 | 11/2017 |
| CA | 3067610 A1 | 7/2020 |

(Continued)

OTHER PUBLICATIONS

Dock Lighting Goes Green with the FT Ultra LED Docklight:, APS Resource, News Release. 1 page.
(Continued)

*Primary Examiner* — Rami Khatib
(74) *Attorney, Agent, or Firm* — Perkins Coie LLP

(57) ABSTRACT

Systems and methods for automatically controlling loading dock equipment, such as in response to a trailer approaching and docking at a docking station, are disclosed. The systems and methods can provide scanning devices and scanning operations which assist with, for example, properly aligning a trailer at a docking station and/or checking an interior area in front of the dock door for obstructions. The systems and methods can also transmit messages between components of the system and/or to users of the system regarding the status of components of the systems and/or the status of the overall docking process.

27 Claims, 12 Drawing Sheets

Related U.S. Application Data continuation of application No. 15/305,296, filed as application No. PCT/IB2015/000698 on Apr. 30, 2015, now Pat. No. 10,081,504.

(60) Provisional application No. 61/988,081, filed on May 2, 2014.

(51) Int. Cl.
  *A61B 1/05* (2006.01)
  *A61B 1/06* (2006.01)
  *B65G 69/00* (2006.01)
  *B65G 69/28* (2006.01)
  *G05D 1/00* (2006.01)
  *G06V 20/58* (2022.01)
  *H04L 67/12* (2022.01)

(52) U.S. Cl.
  CPC ............ *A61B 1/018* (2013.01); *B65G 69/001* (2013.01); *B65G 69/003* (2013.01); *B65G 69/2805* (2013.01); *B65G 69/2882* (2013.01); *G05D 1/0225* (2013.01); *A61B 1/051* (2013.01); *A61B 1/0676* (2013.01); *A61B 1/0684* (2013.01); *G05D 1/0661* (2013.01); *H04L 67/12* (2013.01)

(58) Field of Classification Search
  CPC .. A61B 1/0676; A61B 1/0684; B65G 69/001; B65G 69/003; B65G 69/2805; B65G 69/2882; G05D 1/0225; G06V 20/584; H04L 67/12
  See application file for complete search history.

(56) References Cited

U.S. PATENT DOCUMENTS

| | | |
|---|---|---|
| 3,635,277 A | 1/1972 | Bahnsen |
| 3,894,571 A | 7/1975 | Hinchliff |
| 4,009,051 A | 2/1977 | Kazis et al. |
| 4,010,571 A | 3/1977 | McGuire et al. |
| 4,286,911 A | 9/1981 | Benjamin |
| 4,476,853 A | 10/1984 | Arbogast |
| 4,590,118 A | 5/1986 | Yatabe et al. |
| 4,625,456 A | 12/1986 | Lafontaine |
| 4,626,983 A | 12/1986 | Harada et al. |
| 4,661,758 A | 4/1987 | Whittaker |
| 4,744,121 A | 5/1988 | Swessel et al. |
| 4,843,373 A | 6/1989 | Trickle et al. |
| 4,936,731 A | 6/1990 | Noble |
| 4,988,254 A | 1/1991 | Alexander |
| 5,026,242 A | 6/1991 | Alexander |
| 5,047,748 A | 9/1991 | Trickle |
| 5,056,847 A | 10/1991 | Stillwell et al. |
| 5,168,262 A | 12/1992 | Okayama |
| 5,168,267 A | 12/1992 | Trickle |
| 5,181,401 A | 1/1993 | Hodan |
| 5,277,240 A | 1/1994 | Epema et al. |
| 5,323,098 A | 6/1994 | Hamaguchi et al. |
| 5,403,142 A | 4/1995 | Stewart |
| 5,495,102 A | 2/1996 | Fine |
| 5,576,533 A | 11/1996 | Tantraporn |
| 5,775,107 A | 7/1998 | Sparkman |
| 5,831,540 A * | 11/1998 | Sullivan ............. B65G 69/2882 700/83 |
| 5,886,863 A | 3/1999 | Nagasaki et al. |
| 5,886,883 A | 3/1999 | Rai |
| 5,898,585 A | 4/1999 | Sirichote et al. |
| 5,915,446 A | 6/1999 | De |
| 6,082,952 A | 7/2000 | Alexander |
| 6,125,582 A | 10/2000 | Mondragon et al. |
| 6,134,835 A | 10/2000 | Krupke et al. |
| 6,179,036 B1 | 1/2001 | Harvey |
| 6,276,744 B1 | 8/2001 | Huber et al. |
| 6,367,259 B1 | 4/2002 | Timm |
| 6,369,462 B1 | 4/2002 | Siri |
| 6,390,245 B1 | 5/2002 | Metz |
| 6,442,897 B1 | 9/2002 | Mullet |
| 6,476,572 B2 | 11/2002 | Lounsbury |
| 6,523,823 B1 | 2/2003 | Bakoledis |
| 6,543,375 B1 | 4/2003 | Sargent et al. |
| 6,663,527 B2 | 12/2003 | Phelan et al. |
| 6,781,516 B2 | 8/2004 | Reynard et al. |
| 6,787,259 B2 | 9/2004 | Colborn et al. |
| 6,810,817 B1 | 11/2004 | James |
| 6,812,849 B1 | 11/2004 | Ancel |
| 6,917,298 B2 | 7/2005 | Romano et al. |
| 6,972,226 B2 | 12/2005 | Deppe et al. |
| 6,975,226 B2 | 12/2005 | Reynard et al. |
| 7,032,720 B2 | 4/2006 | Jette et al. |
| 7,045,764 B2 | 5/2006 | Beggs et al. |
| 7,119,673 B2 | 10/2006 | Eager et al. |
| 7,162,762 B1 | 1/2007 | Gleason |
| 7,165,486 B2 | 1/2007 | Alexander et al. |
| 7,230,819 B2 | 6/2007 | Muchow et al. |
| 7,254,868 B2 | 8/2007 | Mullet et al. |
| 7,256,703 B2 | 8/2007 | Duvernell et al. |
| 7,264,092 B2 | 9/2007 | Jette |
| 7,274,300 B2 | 9/2007 | Duvernell et al. |
| 7,327,107 B2 | 2/2008 | Mullet et al. |
| 7,333,016 B2 | 2/2008 | Ancel |
| 7,380,375 B2 | 6/2008 | Maly |
| 7,686,061 B2 | 3/2010 | Mullet et al. |
| 7,730,981 B2 | 6/2010 | Mccabe et al. |
| 7,750,890 B2 | 7/2010 | Fitzgibbon et al. |
| 7,864,030 B2 | 1/2011 | Jette |
| 7,956,718 B2 | 6/2011 | Murphy et al. |
| 8,058,970 B2 | 11/2011 | Mullet et al. |
| 8,065,770 B2 | 11/2011 | Proffitt et al. |
| 8,112,949 B2 | 2/2012 | Eungard |
| 8,181,401 B2 | 5/2012 | Eungard |
| 8,286,757 B2 | 10/2012 | Nelson |
| 8,307,589 B2 | 11/2012 | Eungard |
| 8,307,956 B2 | 11/2012 | Andersen et al. |
| 8,345,010 B2 | 1/2013 | Fitzgibbon et al. |
| 8,364,334 B2 | 1/2013 | Au et al. |
| 8,407,842 B2 | 4/2013 | Story et al. |
| 8,410,895 B2 | 4/2013 | Murphy et al. |
| 8,490,669 B2 | 7/2013 | Fletcher et al. |
| 8,497,761 B2 | 7/2013 | Mcneill et al. |
| 8,510,888 B2 | 8/2013 | Eungard |
| 8,528,622 B2 | 9/2013 | Ehrlich |
| 8,547,234 B2 | 10/2013 | Maly et al. |
| 8,590,087 B2 | 11/2013 | Swessel et al. |
| 8,590,674 B2 | 11/2013 | Jette |
| 8,775,710 B1 | 7/2014 | Miller et al. |
| 8,893,764 B2 | 11/2014 | Mascari et al. |
| 8,959,838 B1 | 2/2015 | Marinelli |
| 8,976,006 B2 | 3/2015 | Krupke et al. |
| 8,978,562 B2 | 3/2015 | Nagamine et al. |
| 9,211,889 B1 | 12/2015 | Hoetzer et al. |
| 9,230,419 B2 | 1/2016 | Beggs et al. |
| 9,283,935 B2 | 3/2016 | Fujioka |
| 9,487,984 B2 | 11/2016 | Wachtell et al. |
| 9,517,902 B2 | 12/2016 | Harrington |
| 9,564,072 B2 | 2/2017 | Senfleben et al. |
| 9,623,859 B2 | 4/2017 | Lavoie et al. |
| 9,633,537 B2 | 4/2017 | Beggs et al. |
| 9,656,691 B2 | 5/2017 | Heimberger et al. |
| 9,771,225 B2 | 9/2017 | Stone et al. |
| 9,776,511 B2 | 10/2017 | Brooks et al. |
| 9,777,529 B2 | 10/2017 | Mcneill et al. |
| 9,926,148 B2 | 3/2018 | Hochstein et al. |
| 9,957,121 B2 | 5/2018 | Sveum et al. |
| 10,032,380 B2 | 7/2018 | Mushynski et al. |
| 10,053,904 B2 | 8/2018 | Mcneill et al. |
| 10,081,504 B2 | 9/2018 | Walford et al. |
| 10,096,187 B2 | 10/2018 | Deneen et al. |
| 10,106,342 B2 | 10/2018 | Avalos |
| 10,113,352 B2 | 10/2018 | McNeill et al. |
| 10,227,190 B2 | 3/2019 | Brooks et al. |
| 10,358,858 B2 | 7/2019 | Lietz et al. |
| 10,435,936 B2 | 10/2019 | Lietz et al. |

(56) References Cited

U.S. PATENT DOCUMENTS

| Patent/Pub No. | Date | Inventor |
|---|---|---|
| 10,494,205 B1 | 12/2019 | Hoofard et al. |
| 10,878,386 B2 | 12/2020 | Hoofard et al. |
| 10,947,069 B2 | 3/2021 | Brooks et al. |
| 11,124,372 B2 | 9/2021 | Hoofard et al. |
| 11,142,413 B2 | 10/2021 | Hoofard et al. |
| 11,225,824 B2 | 1/2022 | Hoofard et al. |
| 11,262,747 B2 | 3/2022 | Hoofard et al. |
| 11,305,953 B2 | 4/2022 | Hoofard et al. |
| 11,358,813 B2 | 6/2022 | Walford et al. |
| 11,507,926 B2 | 11/2022 | Hoofard et al. |
| 11,668,131 B2 | 6/2023 | McNeill et al. |
| 2001/0035667 A1 | 11/2001 | Gaeta |
| 2002/0089427 A1 | 7/2002 | Aratani et al. |
| 2003/0167238 A1 | 9/2003 | Zeif et al. |
| 2004/0146384 A1 | 7/2004 | Whelan |
| 2005/0050438 A1 | 3/2005 | Cheung et al. |
| 2005/0102041 A1 | 5/2005 | Duvernell et al. |
| 2005/0102042 A1 | 5/2005 | Reynard et al. |
| 2005/0126081 A1* | 6/2005 | Patel ............... B64G 1/00 52/2.11 |
| 2005/0262549 A1 | 11/2005 | Ritt et al. |
| 2006/0119132 A1 | 6/2006 | Rivers et al. |
| 2006/0137261 A1 | 6/2006 | Maly |
| 2006/0181391 A1* | 8/2006 | McNeill ......... G06Q 10/063114 340/5.61 |
| 2006/0235737 A1 | 10/2006 | Fleurant et al. |
| 2006/0289128 A1 | 12/2006 | Ressel et al. |
| 2007/0062422 A1 | 3/2007 | Wotring |
| 2007/0157614 A1 | 7/2007 | Goldman |
| 2007/0256797 A1 | 11/2007 | Orton et al. |
| 2007/0258798 A1 | 11/2007 | Foster et al. |
| 2007/0283806 A1 | 12/2007 | Morrison |
| 2008/0011799 A1 | 1/2008 | Chang |
| 2008/0018438 A1 | 1/2008 | Ehrlich et al. |
| 2008/0022596 A1 | 1/2008 | Boerger et al. |
| 2008/0124203 A1 | 5/2008 | McDonald |
| 2008/0127435 A1 | 6/2008 | Maly et al. |
| 2008/0143290 A1 | 6/2008 | Chavakula |
| 2009/0013497 A1 | 1/2009 | Squyres et al. |
| 2009/0024979 A1 | 1/2009 | Chessell et al. |
| 2010/0073197 A1 | 3/2010 | Eagleton et al. |
| 2010/0146719 A1* | 6/2010 | Swessel ............. B65G 69/2882 14/71.3 |
| 2011/0075441 A1 | 3/2011 | Swessel et al. |
| 2011/0203059 A1 | 8/2011 | Whitley et al. |
| 2011/0301800 A1* | 12/2011 | Furuno ................ G05D 1/0274 701/25 |
| 2011/0313893 A1 | 12/2011 | Weik |
| 2012/0025964 A1 | 2/2012 | Beggs et al. |
| 2012/0125545 A1 | 5/2012 | Ehrlich |
| 2012/0304558 A1* | 12/2012 | Iglesias Ballester ............... B65G 69/2811 52/173.1 |
| 2013/0024334 A1 | 1/2013 | Kozlay |
| 2013/0038731 A1 | 2/2013 | Brey et al. |
| 2013/0117078 A1 | 5/2013 | Weik et al. |
| 2013/0188050 A1 | 7/2013 | Winget |
| 2013/0261958 A1 | 10/2013 | Herron |
| 2013/0312205 A1 | 11/2013 | Riviere et al. |
| 2013/0327914 A1 | 12/2013 | Mcneill et al. |
| 2013/0332217 A1 | 12/2013 | Mcneill et al. |
| 2014/0075842 A1 | 3/2014 | Mcneill et al. |
| 2014/0137447 A1 | 5/2014 | Mama |
| 2014/0225509 A1 | 8/2014 | Wiegel et al. |
| 2014/0247347 A1 | 9/2014 | Mcneill et al. |
| 2015/0009046 A1 | 1/2015 | Senfleben et al. |
| 2015/0013083 A1 | 1/2015 | Palmersheim |
| 2015/0039552 A1 | 2/2015 | Moyne |
| 2015/0047132 A1 | 2/2015 | Sveum et al. |
| 2015/0047133 A1 | 2/2015 | Sveum |
| 2016/0075526 A1 | 3/2016 | Avalos |
| 2016/0090072 A1 | 3/2016 | Eppley et al. |
| 2016/0104364 A1 | 4/2016 | Brooks et al. |
| 2016/0031482 A1 | 5/2016 | Lavoie |
| 2016/0178382 A1 | 6/2016 | Penna et al. |
| 2016/0288833 A1 | 10/2016 | Heimberger et al. |
| 2016/0362135 A1 | 12/2016 | Xu et al. |
| 2016/0368489 A1 | 12/2016 | Aich et al. |
| 2017/0017392 A1 | 1/2017 | Castaneda et al. |
| 2017/0043967 A1 | 2/2017 | Walford et al. |
| 2017/0044817 A1 | 2/2017 | Mcneill et al. |
| 2017/0073005 A1 | 3/2017 | Jawad et al. |
| 2017/0106794 A1 | 4/2017 | Constantine |
| 2017/0168501 A1 | 6/2017 | Aoki et al. |
| 2017/0174209 A1 | 6/2017 | Lavoie |
| 2017/0205824 A1 | 7/2017 | Nordbruch et al. |
| 2017/0213404 A1 | 7/2017 | Sivalingam et al. |
| 2017/0320685 A1 | 11/2017 | Hoofard et al. |
| 2018/0035606 A1 | 2/2018 | Burdoucci |
| 2018/0278897 A1 | 9/2018 | Seaman et al. |
| 2019/0064835 A1 | 2/2019 | Hoofard et al. |
| 2019/0144218 A1 | 5/2019 | Hoofard et al. |
| 2019/0197318 A1 | 6/2019 | Krishnamurthy et al. |
| 2019/0202646 A1 | 7/2019 | Brooks et al. |
| 2019/0301224 A1 | 10/2019 | Barton |
| 2019/0316403 A1 | 10/2019 | Aiello |
| 2019/0392402 A1 | 12/2019 | Vandergon et al. |
| 2020/0002993 A1 | 1/2020 | Thouin |
| 2020/0018110 A1 | 1/2020 | Lindley et al. |
| 2020/0115948 A1 | 4/2020 | Lietz et al. |
| 2020/0125074 A1 | 4/2020 | Ramos et al. |
| 2020/0133259 A1 | 4/2020 | Van Wiemeersch et al. |
| 2020/0334631 A1 | 10/2020 | Conlon |
| 2021/0238908 A1 | 8/2021 | Ramage et al. |
| 2022/0146269 A1 | 5/2022 | Hoofard et al. |
| 2022/0170311 A1 | 6/2022 | McNeill et al. |
| 2022/0243524 A1 | 8/2022 | Hoofard et al. |
| 2022/0306410 A1 | 9/2022 | Hoofard et al. |
| 2022/0388380 A1 | 12/2022 | Hoofard et al. |
| 2023/0003074 A1 | 1/2023 | Hoofard et al. |

FOREIGN PATENT DOCUMENTS

| | | |
|---|---|---|
| DE | 102004037933 B3 | 2/2006 |
| EP | 2215612 B1 | 8/2012 |
| EP | 2660170 A1 | 11/2013 |
| FR | 2797246 A1 | 2/2001 |
| FR | 2869470 A1 | 10/2005 |
| WO | 2006066013 A2 | 6/2006 |
| WO | 2006076538 A2 | 7/2006 |
| WO | 2008014206 A1 | 1/2008 |
| WO | 2008036087 A1 | 3/2008 |
| WO | 2009070509 A1 | 6/2009 |
| WO | 2010077977 A1 | 7/2010 |
| WO | 2011037839 A1 | 3/2011 |
| WO | 2015023666 A1 | 2/2015 |
| WO | 2015023669 A1 | 2/2015 |
| WO | 2015084167 A1 | 6/2015 |
| WO | 2015166339 A1 | 11/2015 |
| WO | 2016007321 | 1/2016 |
| WO | 2016209141 A1 | 12/2016 |
| WO | 2017100716 A1 | 6/2017 |
| WO | 2019173811 A2 | 9/2019 |
| WO | 2019209773 A1 | 10/2019 |

OTHER PUBLICATIONS

Pentalift introduces industry's first solar powered dock leveler! www.pentalift.com, Jun. 14, 2011, 1 page.

APS&GO—LED Communication System Specification Sheet, APS Resource, For APS1102, Nov. 2009, 2 pages.

Bin et al., Constrained Model Predictive Control for Backing-up Tractor-Trailer System, Proceeding of the 10th World Congress on Intelligent Control and Automation, Jul. 6-8, 2012, Beijing, China, pp. 2165-2170.

Desantis et al., Path-Tracking for Tractor-Trailers with Hitching of Both the On-Axle and the Off-Axle Kind, Proceedings of the 2002 IEEE International Symposium on Intelligent Control, 2002.

Energy Saving Products Brochure, APS Resource, Mar. 2009, 4 pages.

FT Ultra LED Flex Arm Docklight Specification Sheet, APS Resource, Form APS 1168, Nov. 2009, 2 pages.

(56) References Cited

OTHER PUBLICATIONS

Fuchs C et al: "3D pose estimation for articulated vehicles using Kalman-filter based tracking", Pattern Ricognition. Image Analysis, Allen Press, Lawrence, KS, US, vol. 26, No. 1, Jul. 23, 2016 (Jul. 23, 2016), pp. 109-113.
High Impact LED Dock Light Specification Sheet, APS Resource, Form APS1171, Nov. 2009, 2 pages.
International Search Report and Written Opinion dated Oct. 12, 2015; International Application No. PCT/IB2015/000698; 9 pages.
Kelley Company; Vehicle Restraints brochure; 2008 ; 8 pages.
Manual and Automatic Light Communication Systems, User's Manual, Serco, Oct. 2009, 28 pages.
McGovern et al., An Articulated Truck on a Spreadsheet, Level 3, Issue 1, Nov. 2003, 23 pages.
Model G307K2 Kadet 2 Operator Interface with 7" TFT Display, Red Lion Controls, Inc., Nov. 23, 2015, 4 pages.
Oreh et al., A New Method for Directional Control of a Tractor Semi-Trailer, Australian Journal of Basic and Applied Sciences, 6(12): 369-409, 2012.
Rite-Hite Corporation, Rite-Vu Light Communication Systems Brochure, 6 pages [Not dated].
Safety & Lighting Products Brochure, APS Resource, Sep. 2004, 2 pages.
Serco Vehicle Restraints brochure; 2008; 4 pages.
Serco; Loading Dock Solutions brochure; 2008; 8 pages.
Smart Power Systems International GmbH, Web pages for Hybrid DC/AC Power Supply, Jun. 1, 2004.
Tofael Ahamed: "Navigation of an Autonomous Tractor Using Multiple Sensors", Thesis, Feb. 22, 2008 (Feb. 22, 2008), XP055527539, retrieved from the Internet: URL: https ://tsukuba.repo.nii.ac.jp, [retrieved on Nov. 27, 2018], Chapter 9.

\* cited by examiner

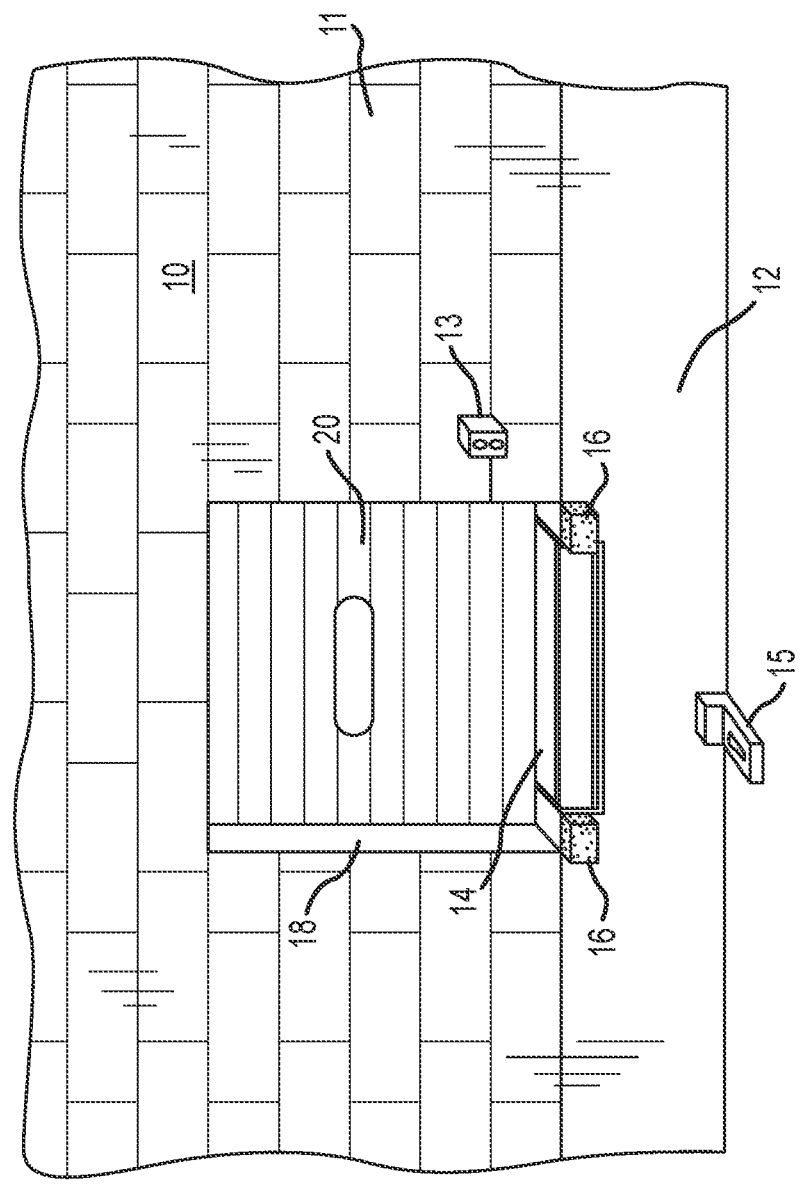

SYSTEMS AND METHODS FOR AUTOMATICALLY CONTROLLING LOADING DOCK EQUIPMENT

CROSS-REFERENCE TO RELATED APPLICATIONS

This application is a continuation of U.S. patent application Ser. No. 16/126,063, filed Sep. 10, 2018, which is a continuation of U.S. patent application Ser. No. 15/305,296, filed Oct. 19, 2016, which is a U.S. National Phase under 35 U.S.C. 371 of International Application No. PCT/IB2015/000698, filed Apr. 30, 2015, which claims priority to U.S. Provisional Application No. 61/988,081, filed May 2, 2014, the entirety of which are hereby incorporated by reference.

TECHNICAL FIELD

The following disclosure relates to systems and methods for automatically controlling loading dock equipment, such as in response to a trailer approaching and docking at a docking station.

BACKGROUND

Warehouse docking stations typically provide a dock door elevated at a certain distance off the ground and an exterior area for a trailer to be backed up to the dock door. The vertical wall extending from the ground to the bottom of the dock door is typically referred to as the dock face. In order to provide for safe and efficient loading and unloading, the trailer typically needs to be aligned so that the rear end of the trailer is parallel with the dock face. The trailer should also be centered with respect to the dock door. Dock face bumpers are typically positioned on the dock face just below the dock door and just inside the left and right edges of the dock door. The trailer is typically backed up to the dock face so that there is little to no space between left and right dock bumpers and the rear end of the trailer. When the trailer is properly positioned, it can be serviced by dock workers using equipment designed to facilitate safe loading and unloading.

Aligning a trailer at a docking station as described above is typically achieved by the driver using rear and/or side view mirrors to manually steer the trailer into the appropriate position. A determination of misalignment during the process of backing the trailer up to the dock bumpers is typically only made when the driver or another individual makes a visual inspection of the trailer position during the docking process, or after the docking process is believed to be completed. In some cases, alignment of the trailer is verified by an individual inside the warehouse. It is often difficult and/or cumbersome for the individual inside the warehouse to notify the outside driver of trailer misalignment.

Once proper alignment of the trailer at the docking station has been achieved and confirmed, a trailer restraint can be engaged to stabilize the trailer and prevent the trailer from moving away from the dock bumpers during loading and unloading. In some cases, an individual is tasked with manually pressing a control button that causes the trailer restraint to engage the trailer after the driver or a warehouse worker has communicated to the individual that the trailer is correctly aligned.

After the trailer restraint is properly engaged, a visual signal (e.g., an illuminated green light) can be provided inside the building to notify dock workers that it is safe to load/unload the trailer. Outside the building, another visual signal (e.g., an illuminated red light) can be provided to warn vehicle drivers against moving the trailer. Steps are then taken to ensure the interior area in front of the dock door is ready for loading and unloading. For example, the interior area in front of the dock door is typically checked to ensure that the area is clear of debris or materials that would obstruct a fork lift loading/unloading the vehicles. Individuals inside the warehouse typically attend to checking the interior area of the dock station, clearing any debris, and communicating that the interior area is ready for loading or unloading. Once the "all clear" message is conveyed by the person tasked with checking the interior area, an individual can then open the dock door, activate a dock leveler, and authorize the fork lift operator to begin the loading or unloading of the trailer.

As is apparent from the above description, some or all of the steps carried out when positioning a trailer at a typical docking station and preparing the area for loading and unloading are carried out manually by individuals. Additionally, various individuals must communicate with one another to confirm that the next step in preparing the trailer for loading and unloading can be initiated. As a result, some current warehouse operations suffer from increased labor costs and/or reduced efficiency. Additionally, human error or shortcutting can lead to time delays and damage to loading dock equipment.

BRIEF DESCRIPTION OF THE DRAWINGS

FIG. 1A is a perspective view of the exterior of a docking station at which one or more components of a dock equipment control system configured in accordance with an embodiment of the present disclosure can be installed.

DETAILED DESCRIPTION

Figure 1B:
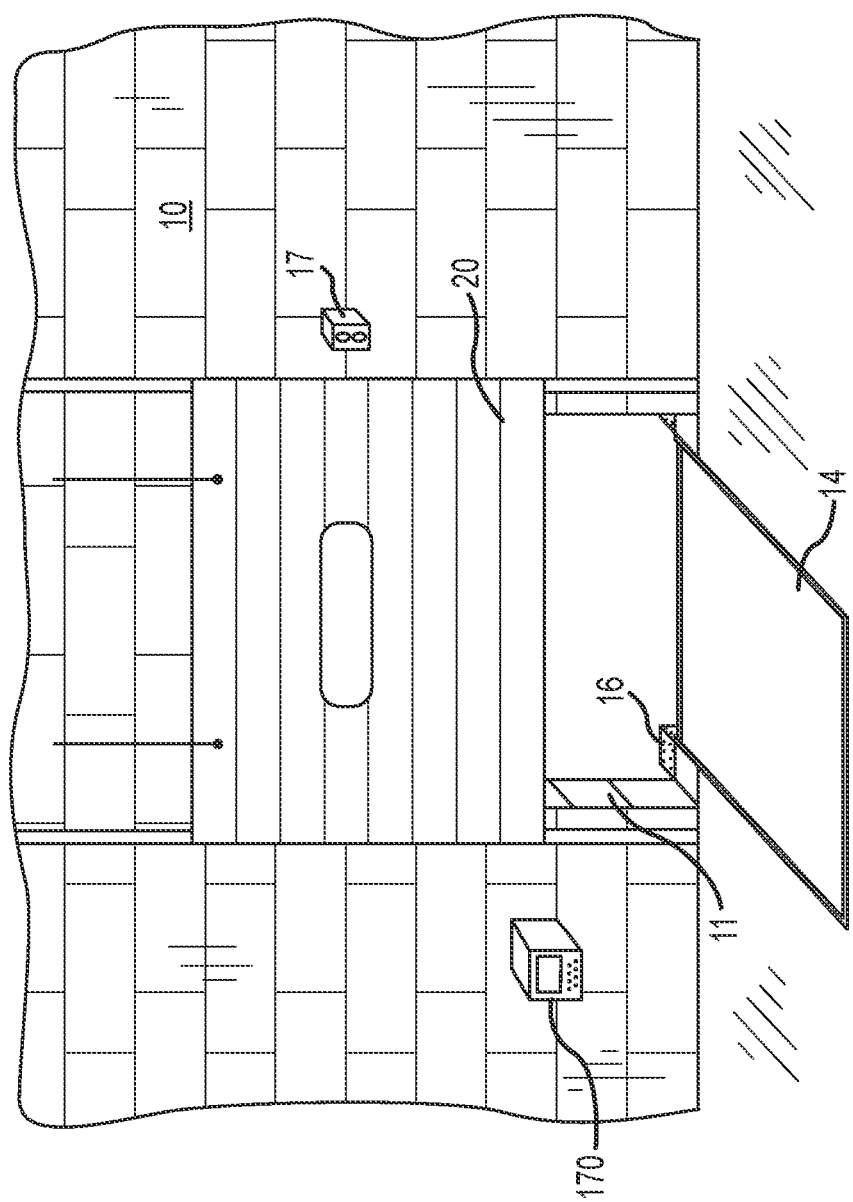
FIG. 1B is a perspective view of the interior of a docking station at which one or more components of a dock equipment control system configured in accordance with an embodiment of the present disclosure can be installed.

Certain details are set forth in the following description and FIGS. 1A-4 to provide a thorough understanding of various embodiments of this disclosure. Those of ordinary skill in the relevant art will appreciate, however, that the technology disclosed herein can have additional embodiments that may be practiced without several of the details described below and/or with additional features not described below. In addition, some well-known structures and systems often associated with dock equipment control systems, apparatuses, and methods have not been shown or described in detail below to avoid unnecessarily obscuring the description of the various embodiments of this disclosure.

In the Figures, identical reference numbers identify identical, or at least generally similar, elements. Many of the details, dimensions, angles, and other features shown in the Figures are merely illustrative of particular embodiments of the disclosure. Accordingly, other embodiments can have other details, dimensions, angles, and features without departing from the spirit or scope of the present invention. In addition, those of ordinary skill in the art will appreciate that further embodiments of the invention can be practiced without several of the details described below.

FIG. 1A is a perspective view of the exterior of a typical docking station 10 at which one or more components of a dock equipment control system configured in accordance with an embodiment of this disclosure can be installed. The docking station 10 typically includes a dock door 20 (e.g., an overhead door) installed in an opening 18 in a building wall 11 at a raised position above the ground. A dock face 12 extends from the ground to the bottom of the building wall 11. The building wall 11 can be set back from the dock face 12 a distance of, e.g., from 6 to 8 inches. The dock leveler 14 is positioned in the opening 18 and can serve as a ramp which, when engaged, provides access between the dock floor and the floor of the trailer positioned at the docking station 10. While not shown in FIG. 1A, the dock station can also include a dock seal, which typically extends around the top and left and right sides of the opening 18 and provides a seal between the building wall 11 and the trailer.

The docking station 10 can also include outside communication lights 13 mounted on the exterior side of the building wall 11 and preferably at a location that allows easy viewing by a driver while a trailer is being positioned at the docking station 10. In some embodiments, the outside communication lights 13 are positioned to the right of the dock door 20 as shown in FIG. 1A so that the outside communication lights 13 can be seen in the side view mirrors of the trailer being positioned at the docking station 10. The outside communication lights 13 can be used to communicate various messages to the driver (or other workers outside of the warehouse), such as whether the trailer can be moved away from the docking station 10.

The docking station 10 can further include a trailer restraint 15. The trailer restraint 15 can be mounted to the dock face 12 near the ground and centered with respect to the dock door 20. The trailer restraint 15 is configured to engage a bar (e.g., a rear impact guard (RIG)) provided at the rear of a trailer, and helps to prevent the trailer from moving away from the dock face 12 during loading and unloading operations.

The docking station 10 can further include a set of dock bumpers 16. The dock bumpers 16 are mounted near the top of the dock face 12 and just outboard of either side of the dock leveler 14. When a trailer backs into the docking station 10, the dock bumpers 16 serves as a signal that the trailer can stop backing up and also prevents the trailer from contacting the building wall 11.

FIG. 1B shows a perspective view of the interior of the docking station 10. As described above, the dock door 20 is movably attached to the interior side of the building wall 11 (via, e.g., door tracks), and the dock leveler 14 can be pivotably mounted in a pit on the building floor so that it can be raised and made to extend in to the trailer parked at the dock. The interior side of the building wall 11 can be used for mounting various components of the dock equipment control system 100 described herein. In some embodiments, for example, a control unit 170 of the dock equipment control system 100 is mounted on the interior side of the building wall 11, such as to the left or right of the dock door 20. Inside communication lights 17 can also be mounted on the interior side of the building wall 11 or directly on the control unit 170. The inside communication lights 17 can include one or more lights of various colors to communicate various messages to the workers inside the warehouse, such as whether loading and unloading of a trailer can begin.

Figure 1C:
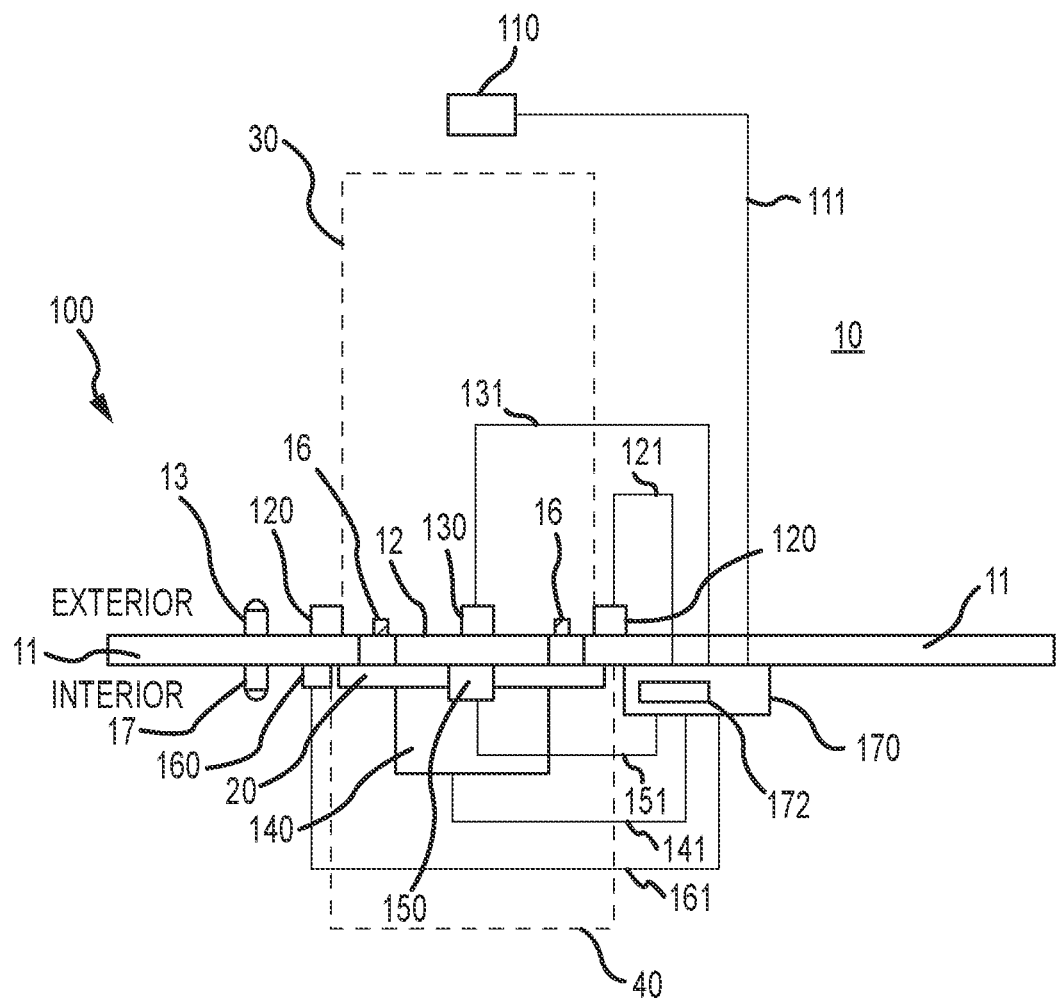
FIG. 1C is a top view schematic diagram illustrating a dock equipment control system configured in accordance with an embodiment of the present disclosure.

FIG. 1C is a schematic diagram illustrating a top view of the docking station 10 equipped with a dock equipment control system 100 configured in accordance with an embodiment of this disclosure. In the illustrated embodiment, the system 100 includes a vehicle detection sensor system 110 (generally located exterior to a building and proximate a docking station), an exterior positioning system 120 (generally located exterior to a building and proximate a docking station), a trailer restraint system 130 (generally located exterior to a building and under a dock door, the trailer restraint system 130 generally including the trailer restraint 15 shown in FIG. 1A and FIG. 1B), a dock leveler system 140 (generally embedded in the floor extending under the dock door), an interior clearance sensor system 150 (generally located inside a building and proximate the dock door), a dock door opening system 160 (generally located proximate the dock door), and a control unit 170. The docking station 10 generally includes a dock door 20, an external trailer docking area 30, and an internal trailer loading area 40. Some of the hardware included in the system 100 is generally typical of hardware included in many loading dock setups, such as the loading docks described in commonly owned U.S. Pat. Nos. 8,893,764; 8,510,888; 8,490,669; 8,407,842; 8,307,589; 8,181,401; 8,112,949; 7,165,486; and 6,082,952, each of which is hereby incorporated herein by reference in its entirety.

As shown in FIG. 1C, the control unit 170 can be electrically connected to each of the vehicle detection sensor system 110 (via link or line 111), the exterior positioning system 120 (via link or line 121), the trailer restraint system 130 (via link or line 131), the dock leveler system 140 (via link or line 141), the interior clearance sensor system 150 (via link or line 151), the inside communication lights 17 (via a link or line not shown in FIG. 1C), the outside communication lights 13 (via a link or line not shown in FIG. 1C), and the dock door opening system 160 (via link or line 161) so that the control unit 170 can receive and send signals to and from each of these components of the dock equipment control system 100. The lines 111, 121, 131, 141, 151, and 161 can generally include electrical lines connecting the individual components of the system, but the lines 111, 121, 131, 141, 151, and 161 can also represent wireless signals sent back and forth between the components of the system 100. The lines connecting the inside communication lights 17 to the control unit 170 and the outside communication lights 13 to the control unit 170 can also generally include electrical lines or wireless signals.

In some embodiments, the vehicle detection sensor system 110 and/or the exterior positioning system 120 can be a part of a general first sensor system that includes one or more sensor systems located exterior of the loading dock door. The first sensor system can include other sensor systems. In some embodiments, the interior clearance sensor system 150 can be a part of a general second sensory system that generally includes one or more sensor systems located interior of the loading dock door. The second sensor system can include other sensor systems. In some embodiments, the trailer restraint system 130, the dock door opening system 160, and/or the dock leveler system 140 can be a part of a dock loading station. The dock leveler system can include other components.

The signals received by the control unit 170 generally convey one or more pieces of information to the control unit 170 regarding, for example, the status of the individual components of the dock equipment control system 100. The control unit 170 processes the information and, based on the input signal received, may send out an instruction signal to any of the individual components of the dock equipment control system 100. Such instruction signals may instruct any of the individual components to, for example, engage or disengage, open or close, etc. The control unit 170 may also receive an input signal and, in response to the input signal, turn on or turn off visual and/or audible signals.

In some embodiments, the control unit 170 receives signals from one or more of the components of the system 100 and provides visual messages via the inside communication lights 17 and/or the outside communication lights 13. As shown in FIGS. 1B and 1C, the outside communication lights 13 can be mounted on an exterior side of the building wall 11 proximate the opening of the door 20 and the inside communication lights 17 can be mounted on an interior side of the building wall 11 proximate the opening. In such configurations, the outside communication lights 13 can convey messages or signals to the driver of the trailer parked at the docking station (or other worker located outside of the warehouse), and the inside communication lights 17 are generally used to convey messages to workers inside of the warehouse. In some embodiments, the inside communication lights 17 and the outside communication lights 13 each contain at least a green light and a red light. The inside communication lights 17 and the outside communication lights 13 can optionally further include a third light, such as an amber light. The individual lights on the outside communication lights 13 and the inside communication lights 117 can be used alone or together to convey various messages or signals based on the status of one or more components of the system 100.

In one example, the controller 170 illuminates the red light on the outside communication lights 13 when the controller 170 receives signals indicating that a trailer is properly aligned at the docking station and the trailer restraint is properly engaged. The illuminated red light indicates to the driver that he or she should not attempt to move the trailer away from the docking station. In conjunction with illuminating the red light on the outside communication lights 13, the controller 170 can also use the information regarding trailer alignment and the trailer restraint to illuminate the green light on the inside communication lights 17. The green light serves as a signal to workers inside the warehouse that it is safe to begin loading or unloading the trailer. When the trailer is not properly aligned at the docking station and/or the trailer restraint is not properly engaged, the controller 170 can instruct the inside communication lights 17 to illuminate a red light to indicate that it is not safe to load or unload the trailer. Similarly, the controller 170 can use this information to illuminate flashing red and green lights on the outside communication lights 13 to indicate to the driver that trailer alignment is not correct and/or the trailer restraint is not properly engaged.

The above example is just one of numerous different ways in which the controller 170 can communicate with the inside communication lights 17 and the outside communication lights 13 to communicate signals to workers inside and outside of the warehouse. As noted, the controller 170 can communicate with both the inside communication lights 17 and the outside communication lights 13 at the same time and using the same information. This enables the inside communication lights 17 and outside communication lights 13 to work in concert to convey a set of related messages to inside and outside workers regarding the conditions inside and/or outside of the warehouse.

The control unit 170 can include any number and type of processing devices and other electronic components capable of working together to receive and deliver signals to various components in accordance with a set of computer readable instructions that, when executed, provide an automatic dock equipment control and communication system. In some embodiments, the control unit 170 includes a programmable logic controller (PLC). The control unit 170 can also include software, including software carried on a computer readable medium, which provides instructions for carrying out and maintaining the automatic docking procedure disclosed herein. The control unit 170 can also include a server for assisting in the transmission of the various signals being sent back and forth between the components of the system 100. The signal may be carried to the control unit 170 via control wiring or through wireless means.

In some embodiments, the control unit 170 includes a graphical user interface (GUI) display 172 (e.g., a liquid crystal display (LCD) or other display screen). The GUI 172 can provide various information, such as textual and/or graphical information, regarding the system 100 for an individual to consult and/or respond to when monitoring and managing the system 100. In one embodiment, for example, the status of all of the components of the system 100 can be displayed by one or more display pages on the GUI 172. The status displayed can be simplified, such as indicating either an "OK" or an "ERROR" status identifier. An "OK" status identifier can indicate that the individual component is operating in accordance with the system protocol and therefore subsequent process steps can take place, while an "ERROR" status identifier can indicate that an individual component is not operating in accordance with the system protocol and therefore no other process steps can take place until the component is checked and the issue remedied. In other embodiments, the GUI 172 provides more detailed information regarding the status of each individual components. For example, regarding the exterior positioning system 120, the GUI 172 can display specific information indicating which way a trailer needs to be steered while a trailer is approaching a docking station (such as, e.g., which way to steer the trailer to correct misalignment). Regarding the interior clearance sensor system 150, the GUI 172 can display specific information indicating how many obstructions have been detected and where each obstruction is located. The system 170 can also provide information audibly via speakers or visually via one or more lights.

The GUI 172 can also include means for automatically and/or manually sending messages regarding the status of various components of the system 100 to one or more different individuals. These communication capabilities can include the ability to send a message (e.g., voice mail, text message, email, electronic message transmitted via a smart phone app, etc.) to a driver positioning a trailer at a docking station. The message can provide real time information on how to re-position the trailer to ensure correct alignment.

Similar information and/or messages can be sent to other individuals involved in the loading process regarding other components of the system, such as a yard manager, an operator, or other individuals working within the warehouse. Messages can also be sent to individuals not located at the warehouse. Messages can also be communicated to other systems, such as a Yard Management System (YMS), which may then relay messages to the appropriate person.

In one embodiment, the control unit 170 can also include a user interface having means for manually operating any of the components of the system 100, including individual functions of the components of the system 100. The means can include, for example, buttons, knobs, levers, dials, switches, etc., including both physical and touch screen versions. In some embodiments, the GUI 172 can display an error message indicating a problem with a component of the system. The error message can then be communicated (either verbally by an individual monitoring the GUI 172 or electronically by the GUI 172 itself) to an individual tasked with correcting the error. Once the individual believes the issue is corrected, the GUI 172 can be used to, for example, rerun a scan of an interior area to ensure a detected obstructions has been cleared, or to reinitiate a trailer engagement sequence after a trailer has been repositioned.

The GUI 172 can provided at a variety of different locations and/or in a variety of different forms. In some embodiments, the GUI 172 is located in a centralized location of the warehouse where other monitoring functions are carried out. The GUI can also be positioned near the dock door, including on a wall next to the dock door. The GUI can also be in the form of a hand held or mobile device, such as a smart phone, PDA, or tablet that can be carried throughout the warehouse by, for example, a warehouse manager. The system described herein can also include any number of GUIs, including, for example, a GUI positioned at each dock door of the warehouse.

Turning now to the individual components of the system 100, the vehicle detection sensor system 110 is generally any type of sensor suitable for use in detecting the presence or absence of a particular object from a field of view. Suitable vehicle detection sensors can include, but are not limited to, infrared sensors, laser sensors, microwave sensors, inductive loop sensors, photo sensors, pressure sensors, ultrasonic sensors, sonar sensors, thermal sensors, optical sensors, magnetic sensors, or camera analytics sensors. In some embodiments, the vehicle detection sensor system 110 is configured for sensing the presence or absence of a vehicle in a field of view approaching the docking station 10. In some embodiments, the vehicle detection sensor system 110 is positioned at a location external to the warehouse but proximate an individual docking station 10. For example, as shown in FIG. 1C, the vehicle detection sensor system 110 can be positioned at a distal end of the trailer docking area 30 so that the vehicle detection sensor system 110 senses the trailer as it first moves into the trailer docking area 30. The vehicle detection sensor system 110 can be positioned on the ground or at an elevated position. In some embodiments, the vehicle detection sensor system 110 can be positioned much closer to the dock face than what is shown in FIG. 1C, for example, within two feet of the trailer's final position.

The vehicle detection sensor system 110 is configured to send a signal to the control unit 170 via line 111 when the vehicle detection sensor system 110 detects a trailer entering the trailer docking area 30. The control unit 170 receives this signal and, in some embodiments, responds by sending out a signal to one or more of the other components of the dock equipment control system 100, such as signals that cause other components of the dock equipment control system 100 to engage or disengage. The vehicle detection sensor system 110 can also be designed to continuously transmit a signal to the control unit 170 indicating that no trailer is detected and to stop transmitting the signal when a trailer is detected. In such configurations, the control unit 170 processes the absence of a signal from the vehicle detection sensor system 110 as the event that triggers one or more signals being sent by the control unit 170 to other components of the dock equipment control system 100. In some embodiments, the control unit 170 responds to an indication from the vehicle detection sensor system 110 that a trailer is approaching the docking station 10 by automatically sending a signal to the exterior positioning system 120, which in turn instructs the exterior positioning system 120 to wake from a dormant state and begin scanning for the trailer approaching the docking station.

The exterior positioning system 120 generally includes one or more sensors which can be used to determine if the trailer is aligned correctly during the process of backing the trailer up to the docking station, and/or to determine if the rear end of the trailer is positioned sufficiently close to the dock face 12. Any suitable sensors can be used in the exterior positioning system 120, including, but not limited to, infrared sensors, laser sensors, microwave sensors, inductive loop sensors, photo sensors, pressure sensors, ultrasonic sensors, sonar sensors, thermal sensors, optical sensors, magnetic sensors, camera analytics sensors, etc., which can monitor a field of view that encompasses at least a portion of the trailer docking area 30. The one or more sensors of the exterior positioning system 120 can also be positioned at any suitable locations proximate the trailer docking area 30 and which allow the sensor to detect left/right and rear alignment of the trailer. For example, as shown in FIG. 1C, the exterior positioning system 120 includes two sensors, each positioned on either side of the dock door 20.

Figure 2A:
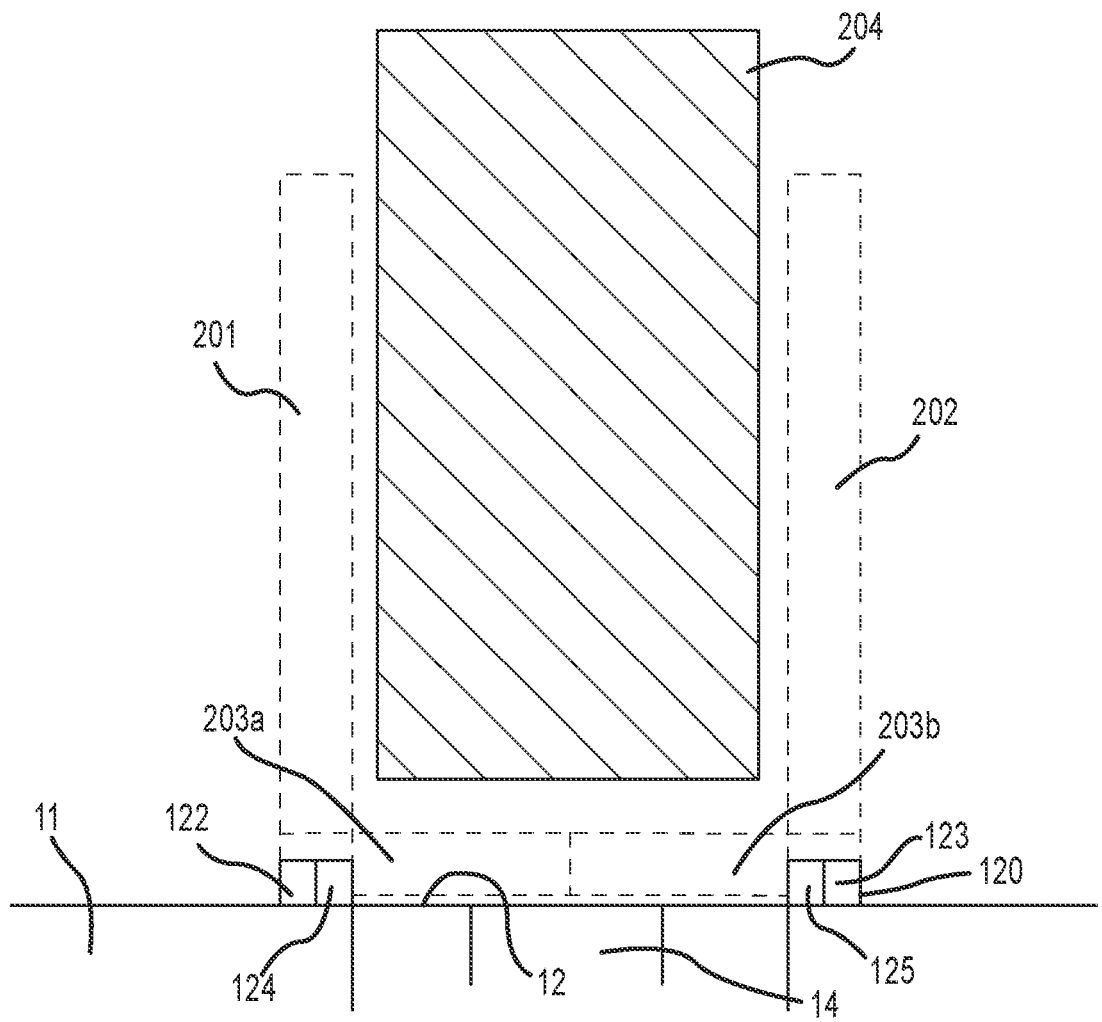
FIGS. 2A-2D are top view schematic diagrams illustrating an exterior positioning system configured in accordance with an embodiment of the present disclosure.

With reference now to FIG. 2A, the scanning regions generated by the exterior positioning system 120 according to one embodiment disclosed herein are shown. The exterior positioning system 120 includes a first left sensor 122, a second left sensor 124, a first right sensor 123, and a second right sensor 125 positioned on either side of the dock door of the docking station. For this embodiment, the first left sensor 122 generates a left scanning zone 201 oriented in a direction perpendicular to and projecting away from the dock face 12 and the second left sensor 124 generates a first rear scanning zone 203a oriented in a direction parallel to the dock face 12 and projecting in a direction towards the second right sensor 125. The first right sensor 123 generates a right scanning zone 202 oriented in a direction perpendicular to and projecting away from the dock face 12. The second right sensor 125 generates a second rear scanning zone 203b oriented in a direction parallel to the dock face 12 and projecting in a direction towards the second left sensor 124. The specific length and width dimensions of the scanning zones 201, 202, 203a, and 203b can be varied according to the specific application and/or preferences of the user. The scanning zones 203a and 203b can each extend the length of the dock door (i.e., overlap one another) or the two scanning zones 203a and 203b can meet in the middle of dock door without any overlap. In some embodiments, a single sensor 124 or 125 may be used in order to create the rear scanning zone. In other embodiments, a rear scan zone is not necessary, in which case second sensors 124 and 125 can be eliminated. For instance, in some embodiments a timer may be used in combination with the other sensors to determine if the trailer is in final position. Movable sensors can also be used, so that a single sensor can scan multiple zones, such as zones 201 and 203*a*, and or 202 and 203*b*.

Figure 2B:
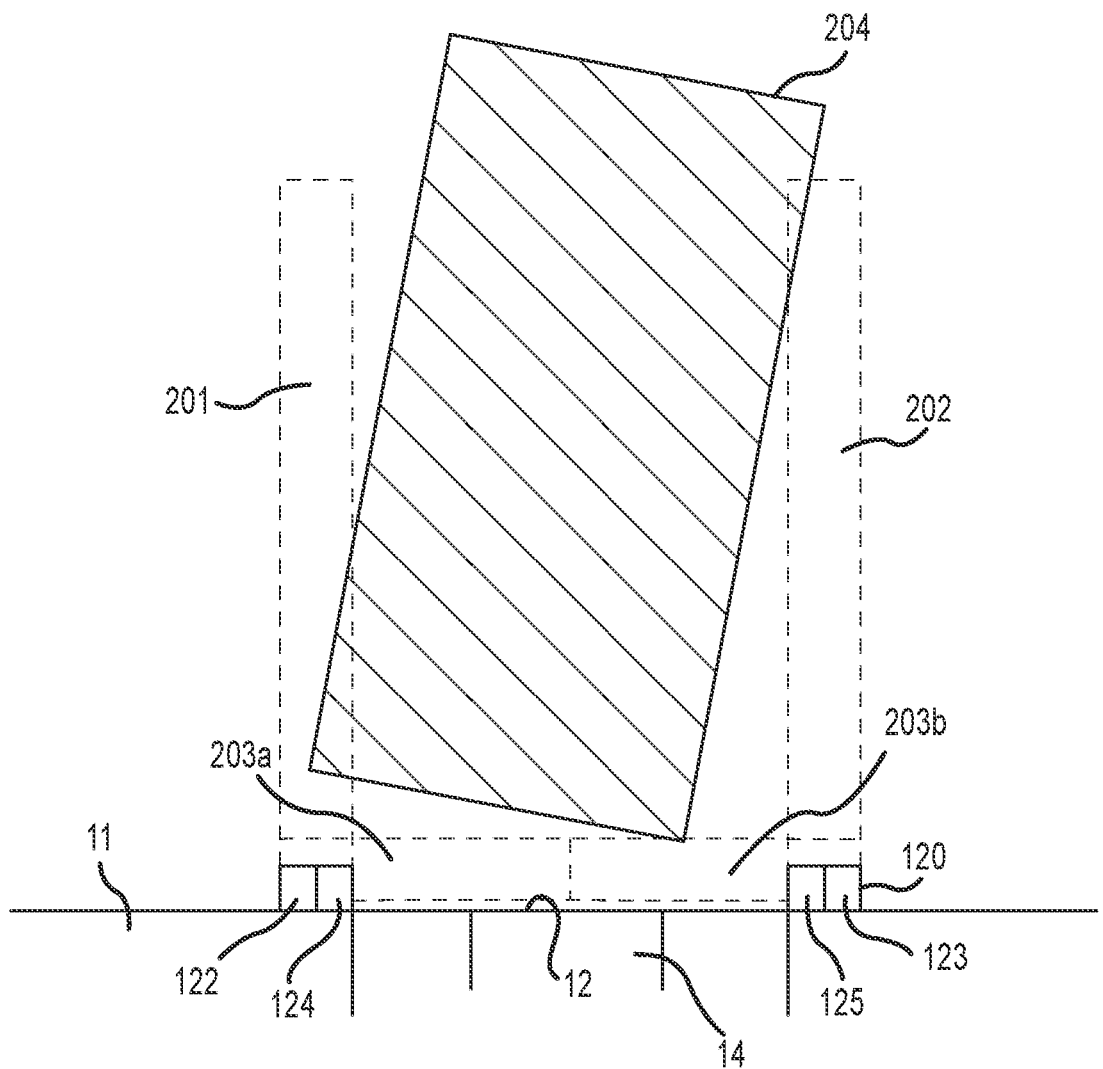

In order to accomplish left/right alignment of the trailer 204 at the docking station 10, the trailer 204 is maneuvered by the driver to stay out of left scanning zone 201 and right scanning zone 202 as the trailer 204 back towards the dock face 12. When the trailer 204 enters into either zone 201, 202, such as shown in FIG. 2B, the sensors 122 and/or 123 detect the presence of the trailer 204 and send a signal to the control unit 170. The control unit 170 can receive this signal and send out a misalignment signal in response. The misalignment signal can be in the form of one or more of several different types of signals. In one embodiment, the misalignment signal is sent out as a message to the driver. The message to the driver can be provided in the form of, for example, an electronic voice message or text message sent to a cell phone. The message can also provide varying levels of information, from a simple message that the trailer 204 is misaligned to a more detailed message indicating the specific way in which the trailer 204 is misaligned and how specifically to correct the misalignment. In another embodiment, the misalignment signal is sent to a light display provided on either side of the dock door, such as one or more lights. The control unit 170 receiving information from the left and right sensors 122, 123 sends signals to these lights to inform the driver of misalignment and, in the case of lights, also provides information to the driver on how to correct the misalignment. For example, when the left sensor 122 detects the presence of the trailer 204 in the left scanning zone 201, a signal is sent to the control unit 170 which in turn sends a signal to the light on the left side of the dock door 20. The light can be an arrow shape pointing in the direction of the center of the dock door 20. Alternatively, the light can have a generic circle shape, but use a designated color to signify which way the trailer should be steered. In either case, the light will light up when receiving the signal from the control unit to thereby indicate to the driver the direction in which the trailer 204 needs to be moved in order to correct the misalignment.

In other embodiments, the control unit can provide audible signals to the driver to assist in the alignment of the vehicle. The audible signals can be in the form of honks or beeps or the like which sound when the trailer enters a left or right scan zone. The audible alarm that sounds when the trailer enters a left or right scan zone can indicate that the trailer needs to be steered out of the scan zone in order to center the trailer and correct the alignment. A separate and distinct audible signal can be provided for rear positioning. The audible signal for rear positioning can sound when the trailer enters the rear scan zone to inform the driver that the trailer has achieved final positioning proximate the left and right dock bumpers.

In some embodiments, in order to accomplish final positioning of the trailer 204 at the docking station 10, the trailer 204 is maneuvered by the driver until the rear end enters the first and/or second rear scanning zone 203*a*, 203*b*. So long as the trailer 204 remains outside of rear scanning zones 203*a*, 203*b*, rear alignment of the trailer 204 is not accomplished. When the trailer 204 enters into rear scanning zone 203*a*, 203*b*, the sensors 124 and/or 125 detect the presence of the trailer 204 and send a signal to the control unit 170. The control unit 170 can receive this signal and send out an alignment message or signals in response. The alignment signal can be in the form of one or more of several different types of signals. In one embodiment, the alignment signal is sent out as a message to the driver. The message to the driver can be provided in the form of, for example, an electronic voice message or text message sent to a cell phone. In another embodiment, the alignment signal is sent to lights provided proximate the dock door, such as green and red lights. The control unit 170 receiving information from the left and right sensors 124, 125 sends signals to these lights to inform the driver of whether additional rearward movement is required (i.e., the green light remains on) or whether rearward movement of the trailer can be stopped (i.e., the green light turns off and the red light turns on). Audible signals can also be used, such as a horn or beep that sounds when final positioning is achieved.

Figure 2C:
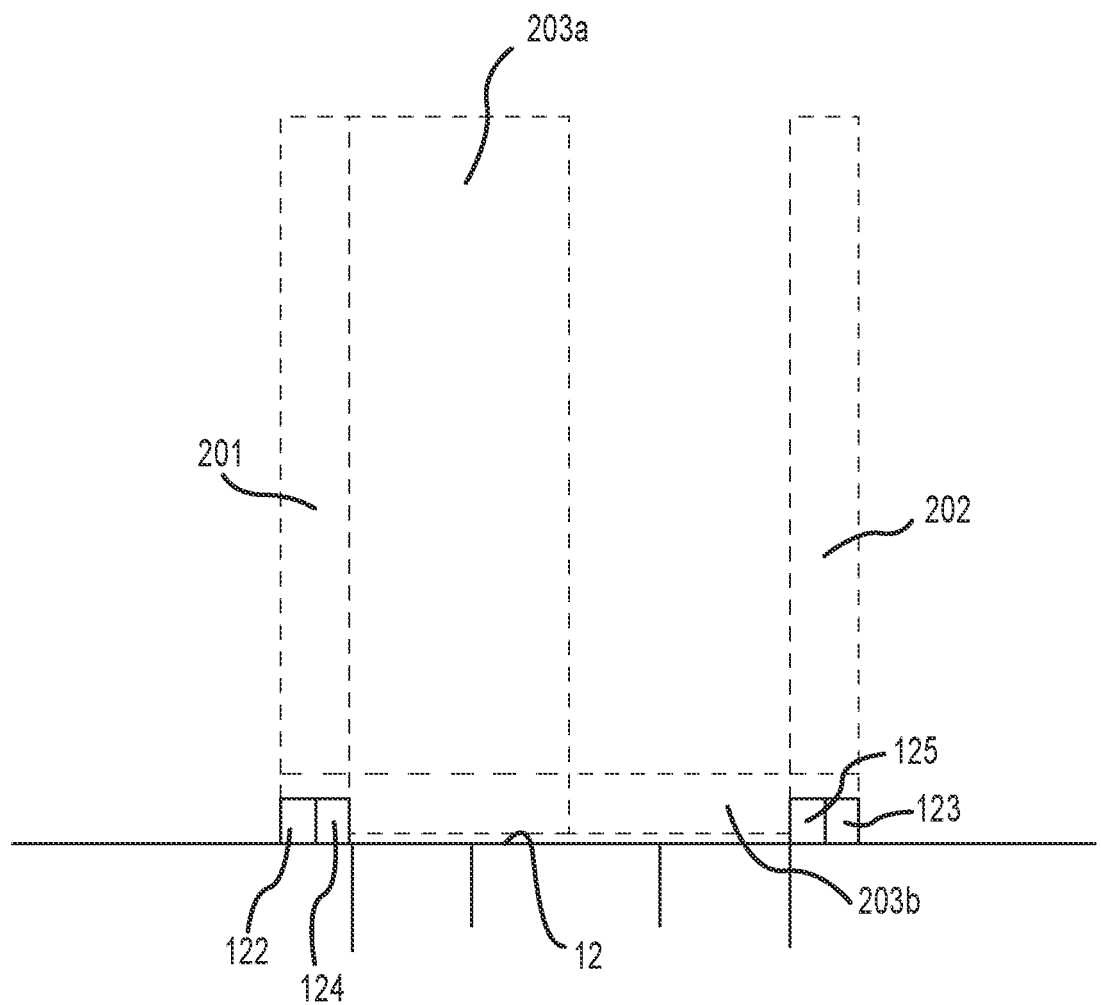

In one embodiment, the rear scanning zones 203*a* and 203*b* are provided with different widths away from the dock face 12 as shown FIG. 2C. Such a configuration allows for a "first check point" scanning zone (e.g., 203*a*) a certain distance away from the dock face 12 and a second scanning zone (e.g., 203*b*) that determines if the trailer is sufficiently close to the dock face 12. Proper rear positioning is only accomplished when the trailer 204 enters the "thinner" scanning zone 203*b*, but the "first check point" scanning zone 203*a* can help to ensure the proper alignment of the trailer is accomplished earlier in the backing up process.

Alternatively, the rear scan zones are not required and instead, the dock bumpers 16 (FIG. 1A) can be used to achieve trailer final position. In other words, final positioning of the trailer is known to be achieved when the trailer contacts the dock bumpers 16.

Figure 2D:
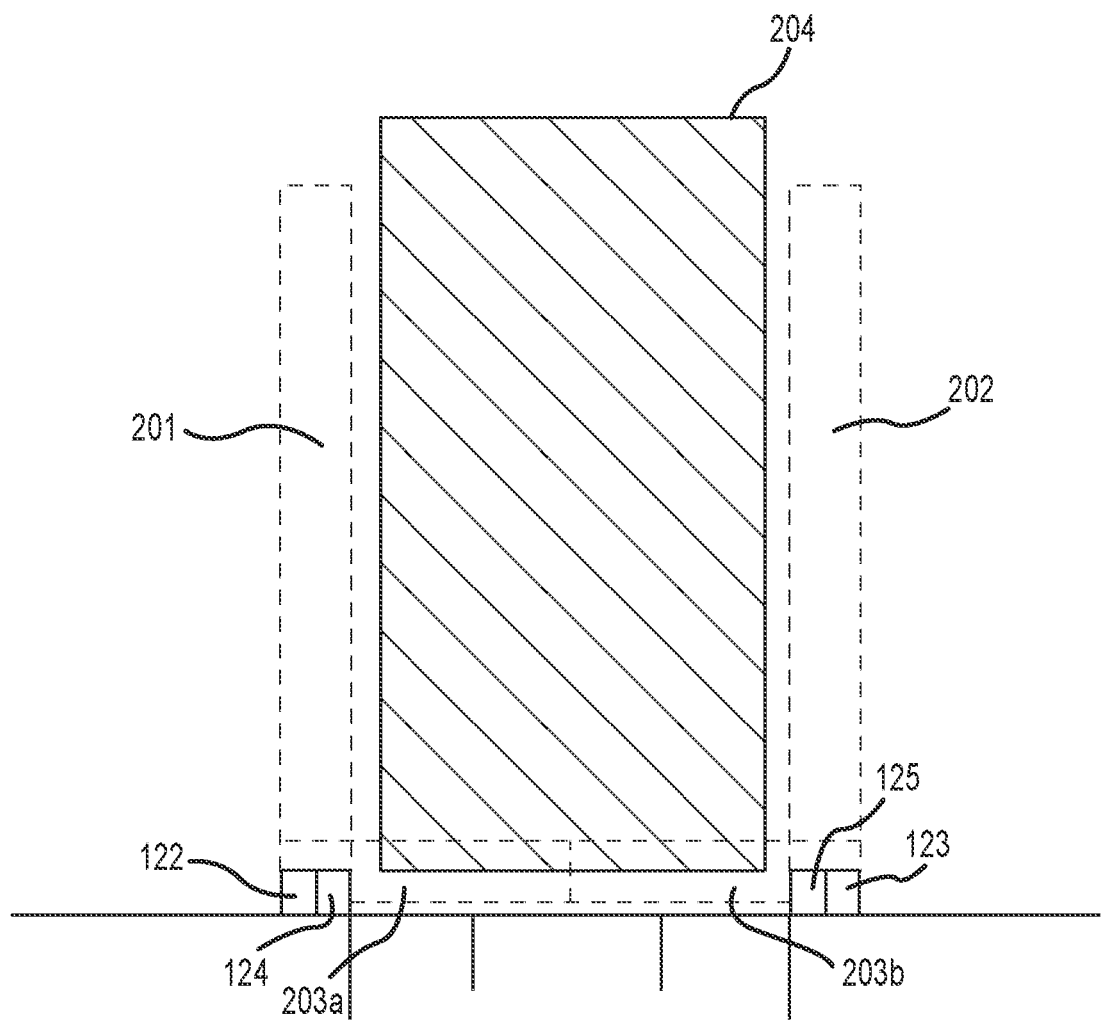
Figure 2E:
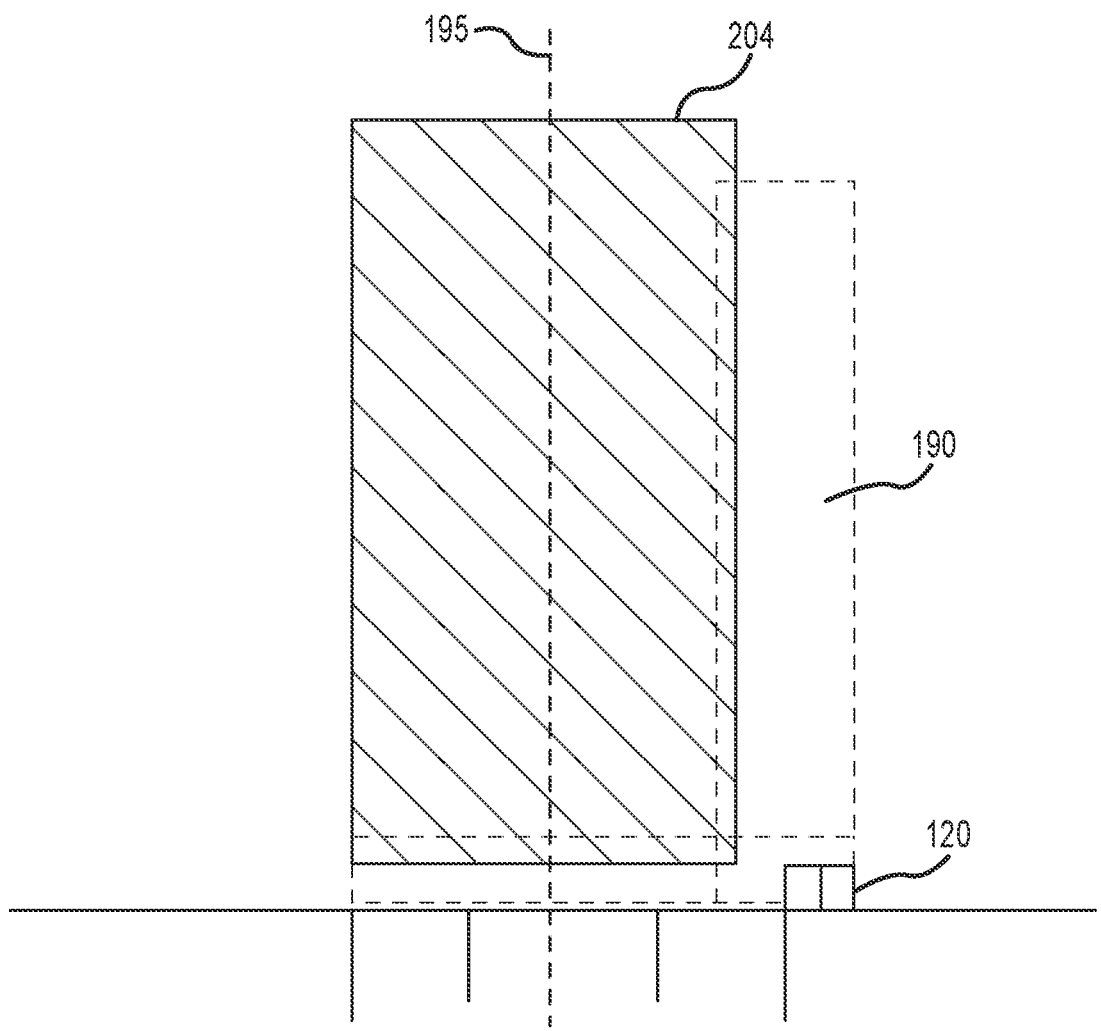
FIG. 2E is a top view schematic diagram illustrating an exterior positioning system configured in accordance with another embodiment of the present disclosure.

With reference now to FIG. 2E, some embodiments provide an exterior positioning system 120 (e.g., a laser sensor) that uses a single sensor that creates a scan zone 190 on either the left or right side of the dock door. This scanning zone 190 (sometimes referred to as a curtain) provides the preferred left or right position of the trailer 204 and monitors whether the trailer 204 is aligned with the curtain 190. When the trailer 204 is aligned with the curtain 190, proper alignment of the trailer is assumed to be accomplished due to the common dimensions of the trailer 190. For example, when a trailer having an 8 foot width is being backed up to the dock bumpers 16 (FIG. 1A), the single sensor 120 can create a curtain 190 that is 6 inches wide and from 45 to 51 inches off the center line 195 of the dock door 20. Alignment of one side of the trailer 204 with the curtain 190 ensures the opposite side of the trailer 204 will also be aligned.

As an alternative to or in conjunction with the exterior positioning system 120 described above, the docking station 10 may include mechanical wheel guides to assist in the proper positioning of the trailer at the docking station 10. In some embodiments, mechanical wheel guides are used to assist with left/right alignment of trailer at the docking station while a modified/simplified version of the exterior positioning 120 is used in order to determine that the rear end of the trailer is sufficiently close to the dock bumpers 16 (FIG. 1A). In other words, the use of mechanical wheel guides can eliminate the need for left scanning zone 201 and right scanning zone 202 and thereby simplify the exterior positioning system 120.

With reference to FIG. 2D, proper alignment of the trailer 204 is accomplished when (1) both the left and right scanning zones 201, 202 do not detect the presence of the trailer, and (2) either or both of the rear scanning zones 203*a*, 203*b* detect the presence of the trailer. Only when both of these conditions are met can the trailer be considered to be in proper alignment at the docking station. When the sensors 122, 123, 124, 125 convey the appropriate signals to the control unit 170 to confirm proper trailer alignment (i.e., no trailer detected in either of scanning zones 201 and 202 and trailer detected in either or both of scanning zones 203a, 203b), the control unit 170 can respond by sending out one or more signals to other components of the dock equipment control system 100 to continue the automated docking process. For example, in one embodiment when the exterior positioning system 120 confirms alignment of the trailer at the docking station, the control unit 170 sends a signal to the interior clearance sensor system 150 to initiate the process of scanning the interior region proximate the dock door for obstructions.

The interior clearance sensor system 150 is configured to scan an interior area 40 (FIG. 1C) in front of the dock door 20 for obstructions that might impede loading or unloading of the trailer at the docking station 10. Clearing the interior area 40 can be especially critical when loading and unloading of the trailer is assisted by the use of automated guided vehicles (AGVs) such as laser guided vehicles (LGVs), fork lifts, etc. AGVs, which use, e.g., lasers or markings to follow paths marked on a warehouse floor, can be disrupted from performing loading and unloading of a trailer if the paths are interrupted or blocked by obstructions. The interior clearance sensor system 150 can generally include one or more sensors capable of identifying an object located within a predetermined area. Any suitable sensors capable of identifying objects in this manner can be used, including but not limited to, infrared sensors, laser sensors, microwave sensors, inductive loop sensors, photo sensors, pressure sensors, ultrasonic sensors, sonar sensors, thermal sensors, optical sensors, magnetic sensors, or camera analytics sensors. As shown in FIG. 1C, the interior clearance sensor system 150 can include a sensor positioned centrally over the top of the dock door 20. This sensor is designed to scan an area in front of the dock door and provide a signal to the control unit 170 if an obstruction is identified.

The size and shape of the area 40 scanned by the interior clearance sensor system 150 can be varied based on the specific application and/or the preferences of the user. In some embodiments, the area scanned has a square or rectangular shape, though other shapes such as semi-circles or triangles could be used. The size of the area scanned can vary across a wide range, with some scanned areas being 40 $ft^2$ or larger. The interior clearance sensor system 150 can also be designed to identify obstructions having varying sizes. In some embodiments, the interior clearance sensor system 150 is capable of identifying any obstructions having a size of as small as, e.g., 1 $in^2$.

As noted above, the interior clearance sensor system 150 is typically initiated upon receiving a signal from the control unit 170, which was sent upon receiving a signal from the exterior positioning system 120 indicating that the trailer is properly aligned at the docking station. Initiation of the interior clearance sensor system can include the interior clearance sensor system 150 beginning a scan of the predetermined area 40 in front of the dock door 20. Depending on the specific system used, the scan of the entire area can be carried out simultaneously, or can take the form of a scan that moves from, for example, left to right across the predetermined area. Upon completion of the scan, the interior clearance sensor system 150 can provide a signal to the control unit 170 which provides information on the results of the scan. In a simplified system, the signal is binary, and indicates only whether an obstruction was identified or not, but does not provide information on how many obstructions were identified or where the obstruction is located within the scanned area. In more sophisticated systems, the signal can provide information on the number of obstructions and/or the location of the obstruction or obstructions.

When the interior clearance sensor system 150 provides a signal to the control unit 170 indicating that an obstruction has been identified, the control unit 170 can convey one or more different types of messages to one or more recipients. In one embodiment, a message indicating an obstruction has been identified is conveyed to a warehouse manager or the like. The message can be conveyed by, for example, a voice message, text message, smart phone app alert, or email to a cell phone or other mobile device. When the control unit 170 sends an obstruction message, the control unit 170 is also generally configured to prevent initiation of any other components of the system 100 (e.g., the dock door opening system 160) until the obstruction has been cleared.

After an obstruction has been identified by the interior clearance sensor system 150, subsequent scanning of the interior area to confirm the obstruction has been removed can be carried out automatically or upon manual initiation. In an automatic configuration, the interior clearance sensor 150 may be programmed to rescan the designated area after a certain time has passed from the obstruction initially being identified. This periodic rescan can be run repeatedly until the obstruction is cleared, after which a signal is sent to the control unit 170 indicating the area is clear and allowing the control unit 170 to reinitiate the process. In another embodiment, the initial scan is run only once, and does not run again until a user manually instructs the scan to be carried out again (such as after this user has cleared the area). The manually initiated rescan will then check the area and, assuming the obstruction has been cleared, send a signal to the control unit 170 indicating that the obstruction has been cleared.

Figure 3A:
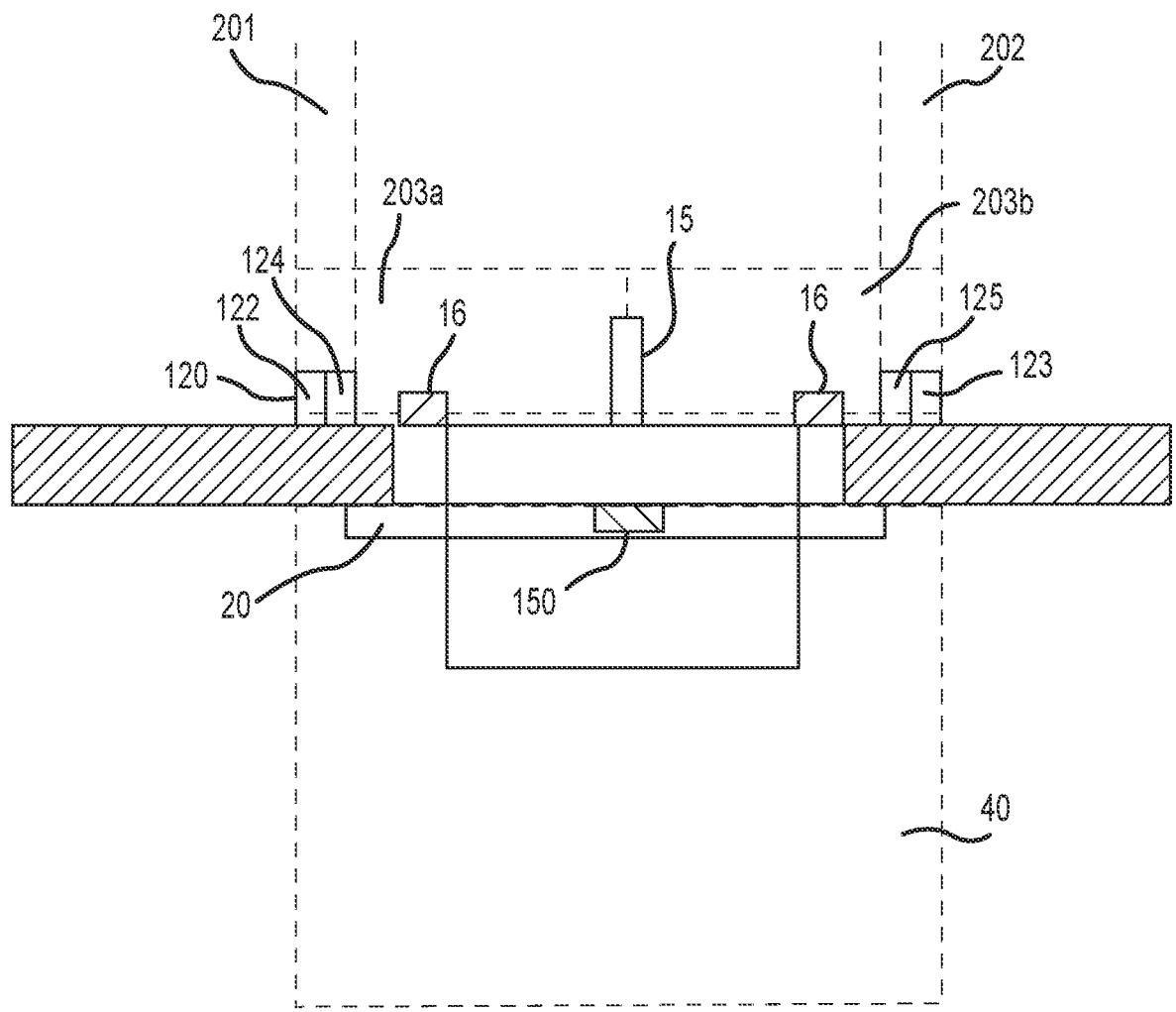
FIGS. 3A and 3B are top and side view schematic diagrams, respectively, illustrating an exterior positioning system and an interior clearance system installed at a docking station and configured in accordance with an embodiment of the present disclosure.
Figure 3B:
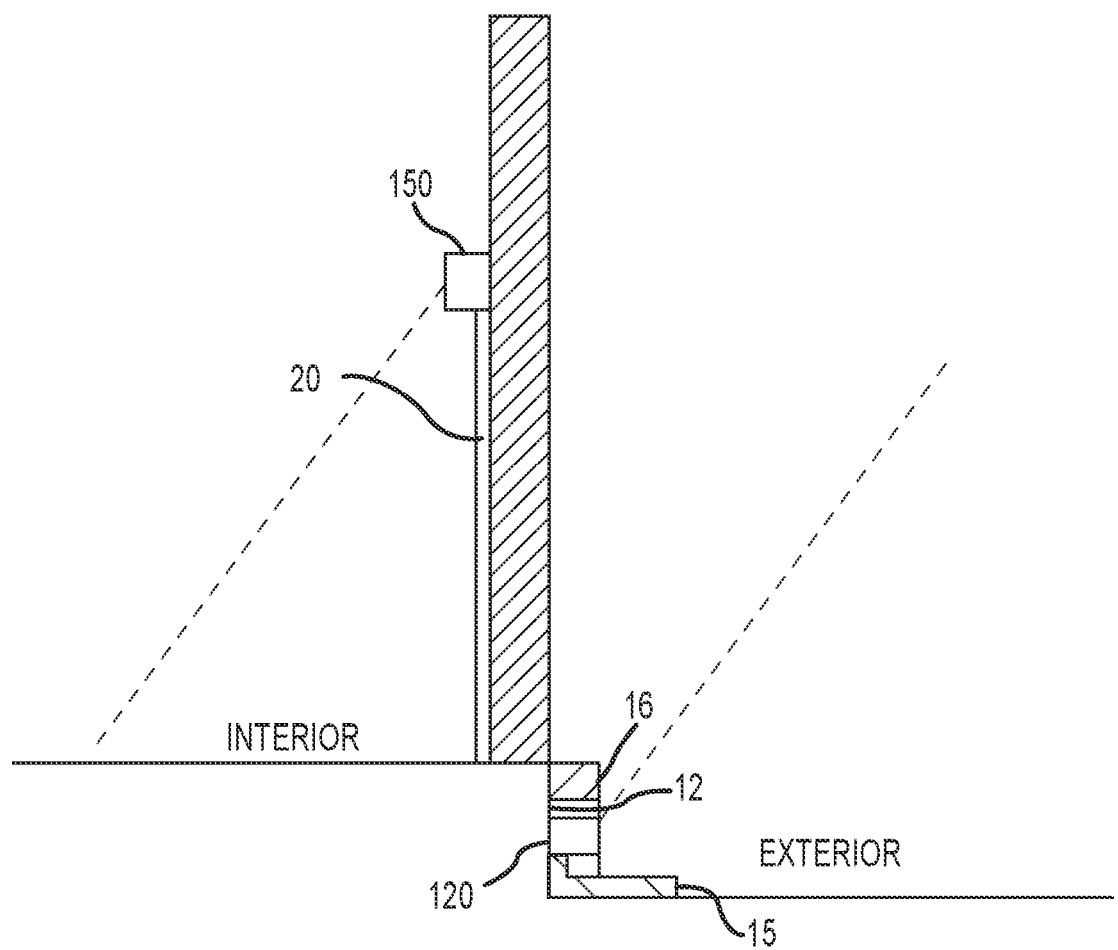
Figure 3C:
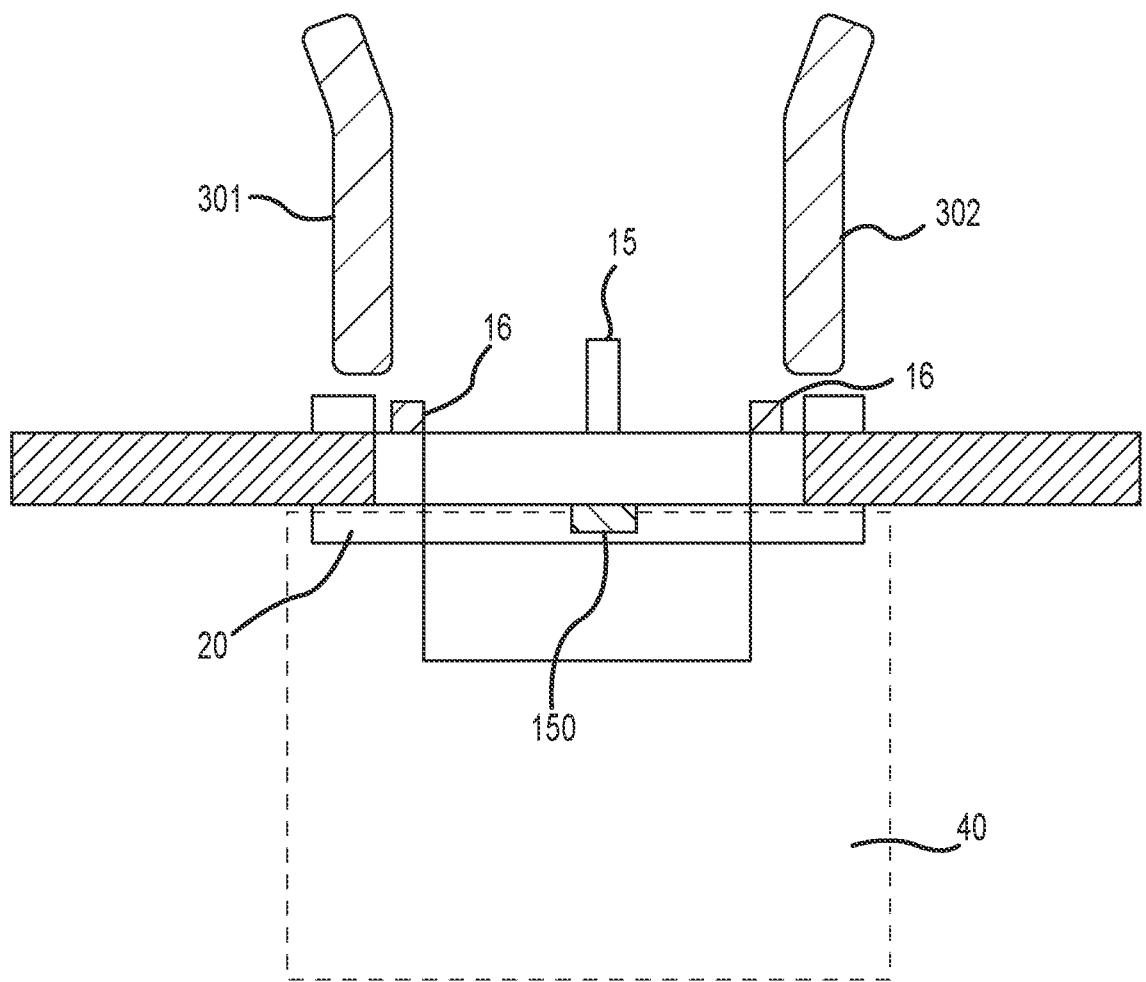
FIG. 3C is a top view schematic diagram illustrating an exterior positioning system and an interior clearance system installed at a docking station and configured in accordance with an embodiment of the present disclosure.

FIGS. 3A through 3C illustrate schematic diagrams of the exterior positioning system 120 and the interior clearance sensor system 150 positioned on opposite sides of the dock door 20, and corresponding scan regions produced by each of the two sensor systems. FIG. 3A illustrates a top view and FIG. 3B illustrates a side view of the two sensor systems. As these views show, the interior clearance sensor system 150 includes a single sensor positioned centrally over the top of the dock door 20 (though the sensor can be located in any other suitable location that permits the sensor to scan the desired interior region). The interior clearance sensor system 150 scans a roughly rectangular shaped area 40 in front of the dock door 20 on the interior of the docking station. The exterior position sensor system 120 includes sensors 122, 124 and sensors 123, 125 positioned on either side of the dock door 20. The sensors work in concert to create scanning zones 201, 202, 203a, and 203b as described in greater detail above. FIG. 3B shows how the sensor of the interior clearance sensor system 150 is located above the dock door 20, while the sensors of the exterior positioning system 120 are positioned on the dock face 12, such as below the bumpers 16 and above the trailer restraint. While FIG. 3B shows the exterior positioning system 120 located in this specific location, the position of the sensors of the exterior positioning system 120 can be anywhere along the height of the exterior wall, provided the sensors of the exterior positioning system 120 can scan the desired regions.

FIG. 3C is a similar top view as FIG. 3A, but includes mechanical wheel guides 301, 302 to carry out left/right alignment of the trailer. The exterior positioning system 120 is still provided in this configuration, but produces only scan regions 203a, 203b for use in ensuring proper rear positioning of the trailer.

Referring back to FIG. 1C, when the interior clearance sensor system 150 transmits a signal to the control unit 170 indicating that the interior area 40 in front of the dock door 20 is clear of obstructions, the control unit 170 can transmit a signal to the trailer restraint system 130 instructing the trailer restraint system 130 to engage the trailer. The trailer restraint system 130 can generally include any type of trailer restraint known to those of ordinary skill in the art. The trailer restraint system 130 generally provides a trailer restraint that engages with the trailer to stabilize the trailer and prevent the trailer from moving away from the dock bumpers 16 during loading and unloading of the trailer. The trailer restraint generally takes the form of a hook or barrier type apparatus that is coupled to the dock face 12 or parking surface proximate the dock door 20. When the trailer restraint is initiated, a hook or barrier extends out of the restraint housing, and creates a barrier to either vehicle wheels or a bar provided under the rear bumper of the trailer (e.g., a Rear Impact Guard or RIG).

The trailer restraint system 130 is configured such that the trailer restraint system 130 can provide a signal to the control unit 170 when the trailer restraint is properly engaged with the trailer. When the trailer restraint system 130 is unable to provide a signal back to the control unit 170 indicating that the trailer restraint is properly engaged (or sends a signal back to the control unit 170 indicating that trailer restraint is not properly engaged), the control unit 170 can convey one or more different types of messages to one or more recipients. In one embodiment, a message indicating the trailer restraint has not properly engaged is conveyed to a warehouse manager or the like. The message can be a text message or voice message to the driver instructing him to manually place wheel chocks under the rear wheel(s) and contact the dock manager when complete. The message can also be conveyed to a manager via a computer display in a control room or the like. The message can be conveyed by, for example, a voice message or text message or email to a cell phone or other mobile device, or to a screen of a computer. When the control unit 170 sends this error message, the control unit 170 is also generally designed to prevent initiation of any other components of the system 100 (e.g., dock door opening system 160) until the trailer restraint has been properly engaged. Similar to the interior clearance sensor system 150 described above, the trailer restraint system 130 can be configured to run repeated checks for proper engagement of the trailer restraint at a predetermined time interval after the initial error message, or only check for proper engagement after an individual manually instructs the check to be performed again (typically after the individual has attended to the trailer restraint and manually corrected the issue). In some embodiments, the trailer restraint system 130 can be configured to run continuous checks for proper engagement of the trailer restraint.

As discussed above, the trailer restraint system 130 is provided at least in part to prevent the trailer from moving away from the dock bumpers 16 during the loading and unloading process. Even with a trailer restraint system 130, some movement of the trailer away from the dock bumpers 16 can take place. Accordingly, the system 100 described herein can include additional components which serve to monitor movement of a trailer away from the dock bumpers 16 and provide an alert when such movement occurs (including whether a trailer restraint is used or not). For example, movement of a trailer away from dock bumpers 16 can be monitored by a component of the system 100 described herein, or can be a stand-alone system which does not require the presence of the other components of the system 100 described herein.

In one embodiment, monitoring the movement of a trailer away from the dock bumpers 16 can be carried out using a sensor system similar or identical to the exterior positioning system 120 described in greater detail above. In such a sensor system, one or more sensors are used to create a scan zone located directly in front of the dock bumpers 16 (similar or identical to rear scan zones 203*a*, 203*b* discussed above). The scan zone can have a relatively narrow depth (distance away from the dock bumpers) such that trailer is only detected in the scan zone when the trailer is located directly against the dock bumpers or a small allowable distance away from the dock bumpers. When the trailer is inside of this zone, the trailer is considered to be in the desired loading position. If the trailer begins to move away from the dock door, the trailer will move out of the scan zone. At this point, the sensor system provides a message to a control unit to provide an alert that the trailer has moved away from the dock bumpers. The control unit may then relay this message to the appropriate person, such as through the use of a messaging system as described above or through a GUI as described above, at which point steps can be taken (such as an audible or visual alarm to notify people on the trailer or nearby) so that the condition may be remedied. When a sensor system monitoring the movement of a trailer away from the dock bumpers is used in conjunction with the system 100 described herein, the sensor system can include one or more of the exterior positioning system 120, the trailer restraint system 130, and the control unit 170 to carry out the function.

When the system 100 described above is used in conjunction with a trailer restraint system 130, the scan system can beneficially help to monitor the development of various issues, such as the development of hook pinch. Hook pinch can occur when a trailer restraint is engaged with a trailer and the trailer moves away from the dock bumpers such that the RIG or vehicle tire(s) begins to contact and pull against the trailer restraint. In some cases, the pressure applied by the trailer on the trailer restraint is sufficiently great that the trailer restraint cannot disengage without the trailer first being moved back toward the dock bumpers. The scan system described above can be an improvement over previously known trailer restraints that monitor hook pinch, because the scan system does not require a specialized trailer restraint with pressure sensors to assess and remedy hook pinch. The scan system described herein can be retrofitted on virtually any existing docking station and does not require the purchase and installation of a new trailer restraint having a pressure sensor. Logic can be programmed into the dock equipment control system 100 such that when the system 100 attempts to disengage the trailer restraint and fails, a text or voice message can be sent to the driver or a message sent to the dock or yard manager to back up the vehicle (back to the dock bumpers) and the trailer restraint disengage operation can be repeated until successful. Additionally, the scan system described avoids the need for a more complicated and expensive trailer restraint that includes a sensor, which may be more prone to maintenance issues and malfunction.

Other sensor systems for detecting the movement of a trailer away from a dock bumper can also be used. In one embodiment, wheel chocks used to prevent movement of a trailer once positioned at a docking station can be used to monitor movement. The wheel chocks can include, for example, pressure sensors which detect increases in pressure that correlate to movement of a trailer away from the dock bumpers. The wheel chocks may be electrically connected via a link or line to a control unit in order to send a message when such increases in pressure are detected. Similarly, pressure pads located near the dock door can be used to detect movement of the trailer away from the dock bumpers.

Using standard wheel locations on a trailer, the pressure pads may be positioned at locations just in front of where wheels of a trailer will be positioned when the trailer is correctly positioned at a docking station. If the trailer begins to move away from the dock door, the wheels will begin to roll over the pressure pads. When the pressure pads detect this pressure, a message can be communicated from the pressure pads to a control unit, which responds by relaying a message or alert to a user regarding the movement of the trailer away from the dock bumpers.

Referring to the trailer restraint system 130 used in conjunction with the system 100 described herein, when the trailer restraint system 130 provides a signal to the control unit 170 indicating proper trailer restraint engagement, the trailer restraint system 130 sends a signal to the control unit 170 indicating proper trailer engagement has been achieved. Upon receipt of this signal, the control unit 170 can provide a signal to the dock door opening system 160 (FIG. 1C) that causes the opening system 160 to open the dock door. The dock door opening system 160 can include any type of automatic door opening mechanism known to those of ordinary skill in the art.

The dock door opening system 160 can be configured to send signals back to the control unit 170 indicating whether the dock door has been successfully opened. As with previously described components of the system 100, the dock door opening system 160 can provide a signal indicating that the dock door has not properly opened or that the dock door has been properly opened. When a signal is transmitted indicating the dock door has not been properly opened, the control unit 170 can convey error messages as described above. The dock door opening system 160 can also continue to check for correction of the error until the door has been properly opened, or can recheck for correction of the issue only after manually instructed to do so. Having received the error message from the dock door opening system 160, the control unit 170 can prevent the initiation of any other components of the system until the error is resolved.

Once the opening system 160 confirms the door 20 is opened properly, the door opening system 160 conveys a signal to the control unit 170 informing the control unit 170 that the dock door 20 is open. At this point, the control unit 170 can transmit a signal to the dock leveler system 140 that instructs or otherwise causes the dock leveler system 140 to initiate. The dock leveler system 140 can include any type of suitable dock leveler known to those of ordinary skill in the art. The dock leveler generally includes an adjustable ramp that provides a smooth transition from the interior area in front of the dock door to the interior floor of the trailer bed, such as in situations where the interior floor in front of the dock door is higher or lower than the interior floor of the trailer bed.

As with the other components of the system 100 described herein, the dock leveler system 140 is capable of transmitting a signal to the control unit 170 indicating whether or not the dock leveler has been properly positioned. When the dock leveler is not properly positioned, the signal sent to the control unit 170 can result in the control unit 170 sending an error message as described in detail above. The dock leveler system 140 can repeatedly check for correction of the issue or be instructed to manually recheck the dock leveler position. While the dock leveler system 140 communicates to the control unit 170 that the dock leveler is not properly positioned, the control unit 170 can prevent engagement of any other components in the system 100.

Once proper positioning of the dock leveler in the trailer has been confirmed, the dock leveler system 140 can convey this message to the control unit 170 for appropriate processing. In some embodiments, proper positioning of the dock leveler is the end of the docking station preparation process and the control unit 170 therefore does not communicate any new signals directing further operation of the components in the system 100. In one embodiment, the control unit 170 is in communication with a separate system designed to run and operate the loading and unloading of the trailer, such as a warehouse management system or a loading system, for example Automatic Guided Vehicles (AGV). In such embodiments, the control unit 170 can transmit a signal to this separate system which indicates the dock station is ready for loading or unloading. The control unit 170 can also send a signal that directly initiates the separate loading system, or send a message to an individual, such as a warehouse manager, which informs that individual that the dock station is prepared. The individual can then take further steps to initiate the separate process, such as through manual initiation.

The system 100 has generally been described above in connection with a specific dock station preparation process. However, those of ordinary skill in the art will understand that the system 100 may also function using a different sequence of steps without departing from the invention disclosed herein. For example, in the system 100 described above, the interior clearance sensor system 150 carries out an interior scan prior to the trailer restraint system 130 being engaged. The system 100 can easily be modified such that the trailer restraint system 130 is engaged prior to or at the same time as the interior clearance sensor system 150 being engaged. Other reordering and/or omitting of steps can also be carried out, and the instant disclosure contemplates these alternate embodiments.

In the embodiments described above, various steps of the process may include the communication of a message to, for example, an individual or a GUI display screen of a user device (e.g., a user-computer, hand-held device such as a smart phone, etc.), indicating a status of a component of the system 100. The message can convey information regarding the operational state of the individual components of the system 100, including whether an error has occurred (e.g., an obstruction exists in the interior area, a trailer restraint has not properly engaged, etc.). In some embodiments, one or more components of the system can include means for manually or remotely overriding the individual component so that when an error message is conveyed, the component can be manually operated by an individual to attempt to correct the issue. The means for manually or remotely overriding the component can include, but is not limited to, a user controlled key or a passcode, a barcode reader, a card scanner, a finger print identification system, a user/password authentication, or any other user security identification device or system. This embodiment of the system allows for only certain designated individuals to attend to the correction of various components of the system 100 and also allows for tracking of which individuals are attending to the correction of the identified issue.

Figure 4:
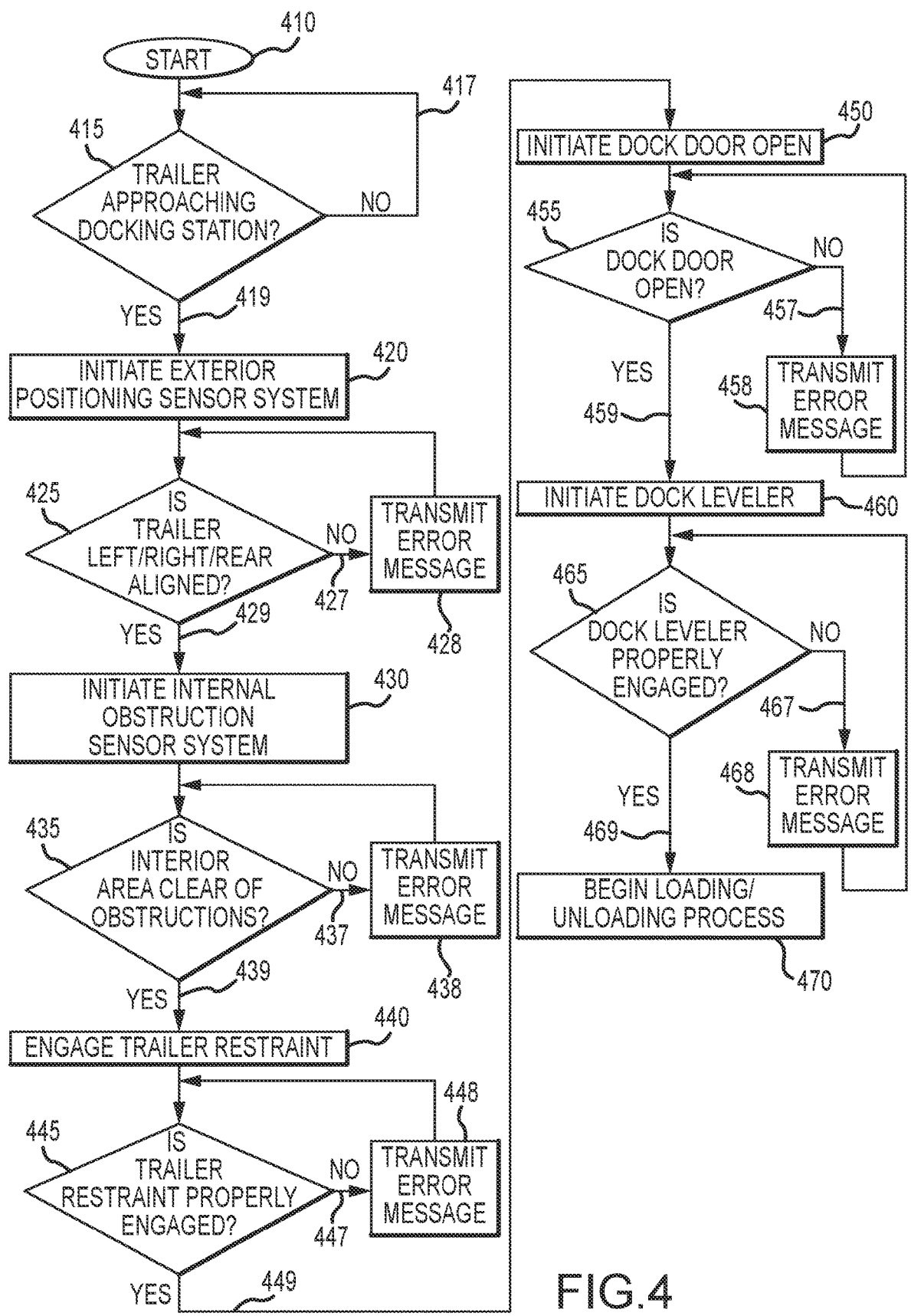
FIG. 4 is a flow chart illustrating a routine for operating a dock equipment control system configured in accordance with an embodiment of the present disclosure.

FIG. 4 is a flow diagram of a technique or routine 400 for carrying out an automated docking procedure according to embodiments of the present disclosure. The automated docking procedure shown is only for exemplary purposes and other procedures are contemplated and fall within the scope of the invention disclosed herein. The procedure illustrated is generally configured such that successful completion of a step must be completed before a second, or subsequent, step in the process can be carried out.

The routine 400 can be carried out by a processor of the control unit 170 according to computer-executable instructions. Those skilled in the relevant art will appreciate that the routine 400 can be practiced with other computer system configurations, including Internet appliances, hand-held devices, wearable computers, cellular or mobile phones, multi-processor systems, microprocessor-based or programmable consumer electronics, set-top boxes, network PCs, mini-computers, local servers, cloud-based servers and the like. The routine 400 can be embodied in a special purpose computer or data processor that is specifically programmed, configured or constructed to perform one or more of the computer-executable instructions explained in detail herein. Indeed, the term "computer" (and like terms), as used generally herein, refers to any of the above devices, as well as any data processor or any device capable of communicating with a network, including consumer electronic goods such as game devices, cameras, or other electronic devices having a processor and other components, e.g., network communication circuitry.

The routine 400 can also be practiced in distributed computing environments, where tasks or modules are performed by remote processing devices, which are linked through a communications network, such as a Local Area Network ("LAN"), Wide Area Network ("WAN") or the Internet. In a distributed computing environment, program modules or sub-routines may be located in both local and remote memory storage devices. Aspects of the routine described herein may be stored or distributed on computer-readable media, including magnetic and optically readable and removable computer discs, stored as in chips (e.g., EEPROM or flash memory chips). Alternatively, aspects of the routine may be distributed electronically over the Internet or over other networks (including wireless networks). Those skilled in the relevant art will recognize that portions of the routine may reside on a server computer, while corresponding portions reside on a client computer. Data structures and transmission of data particular to aspects of the routine are also encompassed within the scope of the invention.

The process starts 410 when a trailer approaches the docking station. A vehicle detection sensor system detects when a trailer approaches the docking station 415. If the vehicle detection sensor system does not detect a trailer 417, then no subsequent steps are carried out and the process returns to the start 410. If the vehicle detection sensor system does detect a trailer 419, then a command is sent to initiate the exterior positioning system 420 to begin the process of assisting the trailer with the backup procedure.

As the trailer backs up towards the dock bumpers, the exterior positioning system determines whether the trailer is achieving left, right, and/or rear alignment 425. If the exterior positioning system detects that the trailer is not aligned on the left, right, and/or at the rear 427, the exterior positioning system and control unit coordinate to send a message 428 that provides an indication of misalignment, and, in some cases, provides which steps should be taken to remedy the misalignment. This message 428 can be sent to the driver or other individual who can assist with aligning the trailer. After the message 428 is sent, the step of checking for left, right, and/or rear alignment 425 is repeated. When the trailer achieves proper left, right, and rear alignment 429, then a command is sent to initiate the interior sensor system 430 to begin the process of checking the interior area in front of the dock door for any obstructions.

Once initiated, the interior scan is carried out to check for obstructions in the area in front of the dock door 435. If obstructions are found 437, then the interior clearance sensor system coordinates with the control unit to send a message 438 that the area is not clear and, in some cases, also provides information on how many obstructions were identified and/or where the obstructions are located. After the message 438 is sent, the step of scanning the interior area 435 is repeated. When the scan of the interior area 435 indicates that the interior area is clear of obstructions 439, then a command is sent to engage the trailer restraint system 440.

After instruction to engage the trailer restraint 440 is carried out, the trailer restraint system provides feedback as to whether proper engagement was accomplished 445. If the trailer restraint is not properly engaged 447, the trailer restraint system and the control unit coordinate to send a message 448 that indicates the trailer restraint system did not properly engage. As described above, the message can be sent in a variety of formats to one or more recipients, including a driver or yard or dock manager or a screen of a computer. After the message 448 is sent, the step of checking for proper trailer restraint engagement 445 is repeated. When confirmation is obtained that the trailer restraint is properly engaged 449, then a command is sent to initiate a dock door opening procedure 450.

After instruction to open the dock door 450 is carried out, the dock door system provides feedback as to whether the dock door was successfully opened 455. If the dock door does not successfully open 457, the dock door system and the control unit coordinate to send a message 458 that indicates the dock door did not successfully open. As described above, the message can be sent in a variety of formats to one or more recipients, including a yard manager or a screen of a computer. After the message 458 is sent, the step of checking for whether the dock door opened successfully 455 is repeated. When confirmation is obtained that the dock door is open 459, then a command is sent to engage the dock leveler 460.

After instruction to engage the dock leveler 460 is carried out, the dock leveler system provides feedback as to whether the dock leveler was successfully engaged 465. If the dock leveler does not properly engage 467, the dock leveler system and the control unit coordinate to send a message 468 that indicates the dock leveler is not properly positioned in a trailer. As described above, the message can be sent in a variety of formats to one or more recipients, including a dock manager or a screen of a computer. After the message 468 is sent, the step of checking for whether the dock leveler properly positioned 465 is repeated. When confirmation is obtained that the dock leveler is properly positioned 469, then a command is sent to initiate the trailer loading and/or unloading process 470. The initiation of a loading and/or unloading process 470 may include communicating with another system that manages loading and unloading processes or may communicate a message to an individual who then takes steps to begin the loading and/or unloading process.

Embodiments of the process described herein can be carried out in reverse in order to prepare the dock station for a loaded or unloaded trailer to pull away from the dock station. Such a process can begin when a signal is provided to the system 100 indicating that the loading or unloading of the trailer has been completed and the trailer is ready to pull away from the dock station. This message can be manually provided to the system, such as an individual providing the instruction through the GUI described above, and/or the message can be conveyed from a separate system, such as a yard management system or a loading system. Receipt of this message causes the control unit to 170 convey a message to the dock leveler system 140 to disengage the dock leveler. Once the dock leveler is properly disengaged, a close dock door instruction can be sent to the dock door system 160, followed by a message to the trailer restraint system 130 to disengage the trailer restraint. The interior clearance sensor system 150 and the exterior positioning system 120 may also be a part of the reverse procedure or may be optionally left out of the reverse system.

As with the process for aligning an approaching trailer at the dock station and readying the dock station for loading or unloading described in detail above, the reverse procedure uses the control system 170 to receive and send various signals regarding the status of the various components of the system. When an individual component of system does not function according to the protocol, the control system 170 is used to convey error messages to one of a variety of systems so that the identified issues can be resolved prior to initiating the next step in the reverse procedure. Additionally, the order of the steps in the reverse procedure need not be carried out in any one specific order and can be varied based on the specific needs of the user.

EXAMPLES

The following examples include additional embodiments of invention described herein.

Example 1. An automated docking system for use with a loading dock station, comprising: a first sensor system configured to detect the presence of a vehicle in an exterior area proximate a loading dock door; a second sensor system configured to detect obstructions in an interior area proximate the loading dock door; and a control unit communicatively coupled with the first sensor system and the second sensor system, the control unit being programmed with computer readable instructions that, when executed: automatically instruct the second sensor system to perform a scan of the interior area when the control unit receives a first signal from the first sensor system indicating that the vehicle is present in the exterior area; and automatically enable operation of at least a portion of the loading dock station when the control unit receives a second signal from the second sensor system indicating that no obstructions have been detected in the interior area.

Example 2. The automated docking system of Example 1, wherein the first sensor system is further configured to assist with aligning the vehicle with a loading dock door.

Example 3. The automated docking system of Example 1, wherein the loading dock station comprises a vehicle restraint system, and wherein automatically enabling operation of at least a portion of the loading dock station includes automatically enabling operation of the vehicle restraint system to engage the vehicle.

Example 4. The automated docking system of Example 1, wherein the loading dock station comprises a dock door opening system, and wherein automatically enabling operation of at least a portion of the loading dock station includes automatically enabling operation of the dock door opening system to open the dock door.

Example 5. The automated docking system of Example 1, wherein the first sensor system comprises at least one sensor configured to scan at least one area proximate and exterior to the loading dock door for the presence of a vehicle within the at least one area.

Example 6. The automated docking system of Example 2, wherein the first sensor system comprises a first sensor located at one side of the loading dock door and a second sensor located at an opposite side of the loading dock door, and wherein the first sensor scans a first area extending perpendicularly away from the loading dock door and the second sensor scans a second area extending perpendicularly away from the loading dock door.

Example 7. The automated docking system of Example 6, wherein the first sensor further scans an area extending parallel to the dock door and towards the second sensor for the presence of a vehicle within the area.

Example 8. The automated docking system of Example 1, wherein the second sensor system comprises at least one sensor configured to scan at least one area proximate and interior of the loading dock door for the presence of obstructions within the at least one area.

Example 9. The automated docking system of Example 8, wherein the second sensor system comprises at least one sensor located above the loading dock door.

Example 10. The automated docking system of Example 1, wherein the first sensor system and the second sensor system each comprise at least one sensor selected from the group consisting of infrared sensors, laser sensors, microwave sensors, inductive loop sensors, photo sensors, pressure sensors, ultrasonic sensors, sonar sensors, thermal sensors, optical sensors, magnetic sensors, camera analytics sensors, or combinations thereof.

Example 11. The automated docking system of Example 2, further comprising at least one communication light located exterior to the loading dock door, and wherein the control unit is further programmed with computer readable instructions that, when executed: instruct the communication light to transmit a first warning message when the vehicle is not aligned with the loading dock door.

Example 12. The automated docking system of Example 11, wherein the control unit is further programmed with computer readable instructions that, when executed: instruct the second sensor system to transmit a second warning message when an obstruction is detected in the interior area.

Example 13. The automated docking system of Example 11, wherein the control unit is further programmed with computer readable instructions that, when executed:
prohibit the second sensor system from scanning the interior area after the first warning message has been transmitted until a user manually instructs the second sensor system to scan the interior area.

Example 14. The automated docking system of Example 12, wherein the control unit is further programmed with computer readable instructions that, when executed: prohibit the vehicle restraint system from engaging a vehicle after the second warning message has been transmitted until a user manually instructs the vehicle restraint system to engage a vehicle.

Example 15. The automated docking system of Example 11, wherein the control unit is further programmed with computer readable instructions that, when executed: after a predetermined period of time, instruct the second sensor system to automatically scan the interior area after the first warning message has been transmitted.

Example 16. The automated docking system of Example 12, wherein the control unit is further programmed with computer readable instructions that, when executed: after a predetermined period of time, instruct the vehicle restraint system to automatically engage with the vehicle after the second warning message has been transmitted.

Example 17. The automated docking system of Example 1, wherein the loading dock station comprises a vehicle restraint system, a dock door opening system, and a dock leveler system, and wherein the control unit is communicatively coupled to the vehicle restraint system, the dock door opening system, and the dock leveler system.

Example 18. The automated docking system of Example 17, wherein the control unit is further programmed with computer readable instructions that, when executed: automatically instruct the dock door opening system to open the dock door when the control unit receives a signal from the vehicle restraint system indicating the vehicle has been engaged by the vehicle restraint system; and automatically instruct the dock leveler system to position the dock leveler inside the vehicle when the control unit receives a signal from the dock door opening system indicating that that the dock door is open.

Example 19. A method for automatically controlling operation of a loading dock station, the method comprising: automatically activating a first sensor system when a vehicle approaches a loading dock door, wherein the first sensor system is configured to detect the presence of the vehicle in an exterior area proximate the loading dock door; automatically activating a second sensor system when the vehicle is present in the exterior area, wherein the second sensor system is configured to scan an interior area of a loading dock door for obstructions; and automatically activating at least a portion of the loading dock station when the scan of the interior area of the loading dock door indicates no obstructions are present in the interior area.

Example 20. The method of Example 19, wherein the first sensor system is further configured to assist with aligning the vehicle with the loading dock door.

Example 21. The method of Example 20, wherein the loading dock station comprises a vehicle restraint system configured to engage a vehicle restraint with the vehicle aligned at the loading dock door.

Example 22. The method of Example 21, further comprising: automatically activating a dock door opening system when the vehicle restraint system engages the vehicle aligned at the loading dock door, wherein the dock door opening system is configured to open a dock door.

Example 23. The method of Example 22, further comprising:
automatically activating a dock leveler system when the dock door is opened, wherein the dock leveler system is configured to position a dock leveler inside a vehicle aligned at the loading dock door.

Example 24. The method of Example 21, further comprising: instructing a communication light to transmit a first warning message when the vehicle is not aligned at the dock door, wherein the communication light is located exterior to the loading dock door.

Example 25. The method of Example 24, further comprising: instructing the second sensor system to transmit a second warning message when an obstruction is detected in the interior area.

Example 26. The method of Example 24, further comprising: prohibiting the second sensor system from scanning the interior area after the first warning message has been transmitted until a user manually instructs the second sensor to scan the interior area.

Example 27. The method of Example 26, further comprising: prohibiting the vehicle restraint system from engaging the vehicle after the second warning message has been transmitted until a user manually instructs the vehicle restraint system to engage the vehicle.

Example 28. The method of Example 24, further comprising: after a predetermined period of time, automatically instructing the second sensor system to scan the interior area after the first warning message has been transmitted.

Example 29. The method of Example 28, further comprising: after a predetermined period of time, automatically instructing the vehicle restraint system to engage the vehicle after the second warning message has been transmitted.

Example 30. The method of Example 25, wherein the second warning message is transmitted in the form of a voice message, a text message, an email, illuminated colored lights, or combinations thereof.

From the foregoing, it will be appreciated that specific embodiments of the invention have been described herein for purposes of illustration, but that various modifications may be made without deviating from the scope of the invention.

The invention claimed is:

1. An automated docking system for use with a loading dock station, the loading dock station including a vehicle restraint system, a loading dock door opening system, and/or a dock leveler, the automated docking system comprising:
   a sensor system configured to detect the presence of a vehicle in an exterior area proximate a loading dock door; and
   a control unit communicatively coupled with the sensor system, the control unit being programmed with computer readable instructions that, when executed, cause the control unit to:
      automatically request a readiness status indicative of whether obstructions are present in an interior area proximate the loading dock door when the control unit receives a first signal from the sensor system indicating that a vehicle is present in the exterior area; and
      automatically enable operation of at least a portion of the loading dock station when, in response to requesting the readiness status, the control unit receives a second signal indicating that no obstructions have been detected in the interior area, wherein automatically enabling operation of at least a portion of the loading dock station includes—
         automatically enabling operation of the vehicle restraint;
         automatically enabling operation of the loading dock door opening system; and/or
         automatically enabling operation of the dock leveler.

2. The automated docking system of claim 1, wherein:
the sensor system is a first sensor system, and
the automated docking system further comprises a second sensor system configured to detect obstructions in the interior area, wherein the control unit is configured to receive the second signal from the second sensor system.

3. The automated docking system of claim 2, wherein at least a portion of the second sensor system is operably coupled to an Automatic Guided Vehicle (AGV).

4. The automated docking system of claim 2, wherein the second sensor system is communicatively coupled to a warehouse management system configured to receive information from the second sensor system related to the readiness status, and wherein the warehouse management system is configured to transmit the second signal to the control unit.

5. The automated docking system of claim 1, wherein automatically requesting the readiness status includes transmitting a third signal to a remote unit of the loading dock station prompting an operator to observe whether obstructions are present in the internal area.

6. The automated docking system of claim 5, wherein, if no obstructions are observed in the interior area, operator interaction with the remote unit transmits the second signal via the remote unit to the control unit.

7. The automated docking system of claim 6, wherein the remote unit is a display screen proximate the loading dock station, a display screen remote to the loading dock station, a hand-held device, or a smartphone.

8. The automated docking system of claim 1, wherein automatically enabling operation of at least a portion of the loading dock station includes automatically enabling operation of the vehicle restraint system to engage the vehicle.

9. The automated docking system of claim 1, wherein automatically enabling operation of at least a portion of the loading dock station includes automatically enabling operation of the loading dock door opening system to open the loading dock door.

10. The automated docking system of claim 1, wherein the sensor system comprises infrared sensors, laser sensors, microwave sensors, inductive loop sensors, photo sensors, pressure sensors, ultrasonic sensors, sonar sensors, thermal sensors, optical sensors, magnetic sensors, camera analytics sensors, or combinations thereof.

11. The automated docking system of claim 1, wherein the sensor system is further configured to assist with aligning the vehicle with the loading dock door.

12. The automated docking system of claim 11, wherein the sensor system comprises a sensor located at a side of the loading dock door, and wherein the sensor scans an area extending perpendicularly away from the loading dock door.

13. The automated docking system of claim 11, wherein the sensor system comprises a first sensor located at one side of the loading dock door and a second sensor located at an opposite side of the loading dock door, and wherein the first sensor scans a first area extending perpendicularly away from the loading dock door and the second sensor scans a second area extending perpendicularly away from the loading dock door.

14. The automated docking system of claim 13, wherein the first sensor further scans an area extending parallel to the loading dock door and towards the second sensor for the presence of the vehicle within the area.

15. The automated docking system of claim 11, further comprising a communication light located exterior to the loading dock door, and wherein the control unit is further programmed with computer readable instructions that, when executed, cause the control unit to:
instruct the communication light to transmit a first warning message when the vehicle is not aligned with the loading dock door.

16. The automated docking system of claim 15, the control unit is further programmed with computer readable instructions that, when executed, cause the control unit to:
instruct the communication light to transmit a second warning message when an obstruction is detected in the interior area.

17. An automated docking system for use with a loading dock station, comprising:
a first sensor system configured to detect the presence of a vehicle in an exterior area proximate a loading dock door;
a second sensor system configured to detect obstructions in an interior area proximate the loading dock door, wherein at least a portion of the second sensor system is operably coupled to an Automatic Guided Vehicle (AGV); and
a control unit communicatively coupled with the first sensor system and the second sensor system, the control unit being programmed with computer readable instructions that, when executed, cause the control unit to:
automatically request a readiness status indicative of whether obstructions are present the interior area when the control unit receives a first signal from the first sensor system indicating that a vehicle is present in the exterior area; and
automatically enable operation of at least a portion of the loading dock station when, in response to requesting the readiness status, the control unit receives a second signal from the second sensor system indicating that no obstructions have been detected in the interior area, wherein the second sensor system transmits the second signal via the AGV to the control unit.

18. An automated docking system for use with a loading dock station, the loading dock station including a vehicle restraint system, a loading dock door opening system, and/or a dock leveler, the automated docking system comprising:
a sensor system configured to detect the presence of a vehicle in an exterior area proximate a loading dock door; and
a control unit communicatively coupled with the sensor system, the control unit being programmed with computer readable instructions that, when executed, cause the control unit to:
receive a first signal from the sensor system indicating that a vehicle is present in the exterior area;
automatically transmit a second signal to a warehouse management system requesting a readiness status indicative of whether obstructions are present in an interior area proximate the loading dock door;
receive a third signal from the warehouse management system with information related to the readiness status; and
automatically enable operation of at least a portion of the loading dock station if the third signal indicates that no obstructions have been detected in the interior area, wherein automatically enabling operation of at least a portion of the loading dock station includes—
automatically enabling operation of the vehicle restraint system;
automatically enabling operation of the loading dock door opening system; and/or
automatically enabling operation of the dock leveler.

19. The automated docking system of claim 18, wherein:
the sensor system is a first sensor system, and
the automated docking system further comprises a second sensor system configured to detect obstructions in the interior area.

20. The automated docking system of claim 19, wherein the second sensor system is communicatively coupled to the warehouse management system, and wherein the warehouse management system transmits the third signal based on information received from the second sensor system related to the readiness status.

21. The automated docking system of claim 20, wherein at least a portion of the second sensor system is operably coupled to an Automatic Guided Vehicle (AGV).

22. The automated docking system of claim 19, wherein the first sensor system and the second sensor system each comprise infrared sensors, laser sensors, microwave sensors, inductive loop sensors, photo sensors, pressure sensors, ultrasonic sensors, sonar sensors, thermal sensors, optical sensors, magnetic sensors, camera analytics sensors, or combinations thereof.

23. The automated docking system of claim 18, wherein, upon receiving the second signal, the warehouse management system is programmed with computer readable instructions that, when executed cause the warehouse management system to transmit a fourth signal to a remote unit of the loading dock station prompting an operator to check for obstructions in the internal area.

24. The automated docking system of claim 23, wherein operator interaction with the remote unit transmits information related to the readiness status of the interior area via the remote unit to the warehouse management system.

25. The automated docking system of claim 18, wherein automatically enabling operation of at least a portion of the loading dock station includes automatically enabling operation of the vehicle restraint system to engage the vehicle.

26. The automated docking system of claim 18, wherein automatically enabling operation of at least a portion of the loading dock station includes automatically enabling operation of the loading dock door opening system to open the loading dock door.

27. The automated docking system of claim 18, further comprising a communication light located exterior to the loading dock door, and wherein the control unit is further programmed with computer readable instructions that, when executed, cause the control unit to:
   instruct the communication light to transmit a warning message if the third signal indicates an obstruction is detected in the interior area.

* * * * *